United States Patent [19]

Warner et al.

[11] Patent Number: 4,717,418

[45] Date of Patent: * Jan. 5, 1988

[54] HERBICIDAL CYCLOHEXANE-1,3-DIONE DERIVATIVES

[75] Inventors: Richard B. Warner, Ringwood; Alexander Serban, Doncaster; Keith G. Watson, Box Hill North; Graham J. Bird, North Melbourne; Lindsay E. Cross, Maribyrnong; Graeme J. Farquharson, Reservoir, all of Australia

[73] Assignee: ICI Australia Limited, Melbourne, Australia

[*] Notice: The portion of the term of this patent subsequent to May 19, 2004 has been disclaimed.

[21] Appl. No.: 440,592

[22] Filed: Nov. 10, 1982

[30] Foreign Application Priority Data

Nov. 20, 1981 [AU] Australia ............................. PF1635
May 25, 1982 [AU] Australia ............................. PF4137

[51] Int. Cl.⁴ .................... A01N 31/04; A01N 33/08; C07C 131/00; C07C 83/00
[52] U.S. Cl. ............................... 71/98; 564/256; 564/300; 560/20; 560/65; 560/73; 560/107; 560/252; 71/106; 71/107; 71/111; 71/121
[58] Field of Search ................ 564/256, 300; 71/98, 71/106, 107, 111, 121; 560/107, 20, 65, 73, 252

[56] References Cited

U.S. PATENT DOCUMENTS 3,950,420  4/1976  Sawaki et al. ........................ 71/88
3,989,737  11/1976 Sawaki et al. ........................ 71/98

OTHER PUBLICATIONS

Hackh's Chemical Dictionary, McGraw-Hill, publ. 4th ed., (1969), at page 420.

Iwataki, I. et al., *Advances in Pesticide Science*, Part 2, pp. 235–243, Pergamon Press, (1979).

*Primary Examiner*—Natalie Trousof
*Assistant Examiner*—L. Hendriksen
*Attorney, Agent, or Firm*—Cushman, Darby & Cushman

[57] ABSTRACT

The invention concerns novel compounds of the formula I

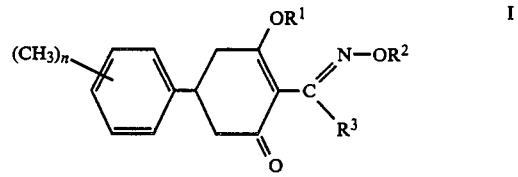

wherein
$R^1$ is selected from hydrogen, alkyl, alkenyl, alkynyl, substituted alkyl, acyl, alkylsulfonyl, benzenesulfonyl, substituted benzenesulfonyl, and an inorganic or organic cation;
$R^2$ is selected from alkyl, alkenyl, alkynyl, substituted alkyl, haloalkenyl and haloalkynyl;
$R^3$ is selected from alkyl, fluoroalkyl, alkenyl, alkynyl and phenyl; and
n is an integer chosen from 2 to 5.

The compounds are cereal selective herbicides and in further embodiments of the invention provides processes for the preparation of compounds of formula I, intermediates useful in the preparation of compounds of formula I, herbicidal compositions containing as active ingredient a compound of formula I, and processes for severely damaging or killing unwanted plants by applying to the plants or to the growth medium of the plants an effective amount of a compound of formula I.

14 Claims, No Drawings

HERBICIDAL CYCLOHEXANE-1,3-DIONE DERIVATIVES

This invention relates to organic compounds having biological activity and in particular to organic compounds having herbicidal properties, to processes for the preparation of such compounds, to intermediates useful in the preparation of such compounds and to herbicidal compositions and processes utilizing such compounds.

The use of certain cyclohexane-1,3-dione derivatives as grass herbicides is known in the art. For example, the "Pesticide Manual" (C R Worthing Editor, The British Crop Protection Council, 6th Edition 1979) describes the cyclohexane-1,3-dione derivative known commercially as alloxydim-sodium (methyl 3-[1-allyloxyimino)-butyl]-4-hydroxy-6,6-dimethyl-2-oxocylcohex-3-ene-carboxylate) and its use as a grass herbicide. This compound is disclosed in Australian Pat. No. 464 655 and its equivalents such as U.K. Pat. No. 1 461 170 and U.S. Pat. No. 3,950,420.

More recently, at the 1980 British Crop Protection Conference ("1980 British Crop Protection Conference—Weeds, Proceedings Vol 1, Research Reports", pp 39 to 46, British Crop Protection Council, 1980), a new cyclohexane-1,3-dione grass herbicide code named NP 55 (2-(N-ethoxybutrimidoyl)-5-(2-ethylthiopropyl)-3-hydroxy-2-cyclohexen-1-one) was announced. This compound is disclosed in Australian Patent Application No. AU-Al-35,314/78 and its equivalents.

As indicated above, both alloxydim-sodium and NP 55 are grass herbicides, that is, herbicides which selectively control the growth of grass weeds (monocotyledonous plants) in broad-leaved crops (dicotyledonous plants).

At the 1978 International Union of Pure and Applied Chemistry Fourth International Congress of Pesticide Chemistry ("Advances in Pesticide Science-Part 2", pp 235-243, Pergamon Press, 1979), in a paper discussing the chemical structure and herbicidal activity of alloxydim-sodium, Iwataki and Hirono made the following disclosure about the herbicidal selectivity between wheat and oats of certain 5-phenyl substituted cyclohexane-1,3-dione derivatives:

"When substituted phenyl groups were introduced at the C-5 position (Table 6), the selectivity between wheats and oats such as *Avena fatua* and *Avena sativa* was observed. The selectivity was found only in the case of para-substituents at the phenyl nucleus and the effect was not found in the case of di- or tri- substitution. Even in the para-substituents, the degree of activity or selectivity was different. The best result was obtained when the methyl group was introduced at the para-position and the hydroxy or the methoxy derivative gave moderately good results."

It has now been found that certain 5-phenyl substituted cyclohexane-1,3-dione derivatives in which the phenyl ring is substituted with more than one methyl group exhibit particularly useful cereal selective herbicidal activity.

Accordingly the invention provides a compound of formula I:

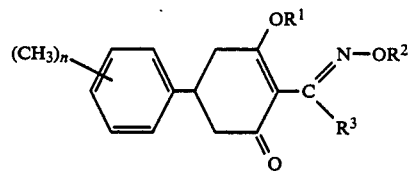

wherein:

$R^1$ is chosen from the group consisting of: hydrogen; $C_1$ to $C_6$ alkyl; $C_2$ to $C_6$ alkenyl; $C_2$ to $C_6$ alkynyl; substituted $C_1$ to $C_6$ alkyl wherein the alkyl group is substituted with a substituent chosen from the group consisting of $C_1$ to $C_6$ alkoxy, $C_1$ to $C_6$ alkylthio, ($C_1$ to $C_6$ alkoxy)carbonyl, phenyl and substituted phenyl wherein the benzene ring is substituted with from one to three substituents chosen from the group consisting of halogen, nitro, cyano, $C_1$ to $C_6$ alkyl, $C_1$ to $C_6$ haloalkyl, $C_1$ to $C_6$ alkoxy and $C_1$ to $C_6$ alkylthio; $C_1$ to $C_6$ (alkyl) sulfonyl; benzene sulfonyl; substituted benzenesulfonyl wherein the benzene ring is substituted with from one to three substituents chosen from the group consisting of halogen, nitro, cyano, $C_1$ to $C_6$ alkyl, $C_1$ to $C_6$ haloalkyl, $C_1$ to $C_6$ alkoxy and $C_1$ to $C_6$ alkylthio; an acyl group; and an inorganic or organic cation;

$R^2$ is chosen from the group consisting of: $C_1$ to $C_6$ alkyl; $C_2$ to $C_6$ alkenyl; $C_2$ to $C_6$ haloalkenyl; $C_2$ to $C_6$ alkynyl; $C_2$ to $C_6$ haloalkynyl; substituted $C_1$ to $C_6$ alkyl wherein the alkyl group is substituted with a substituent chosen from the group consisting of halogen, $C_1$ to $C_6$ alkoxy, $C_1$ to $C_6$ alkylthio, phenyl and substituted phenyl wherein the benzene ring is substituted with from one to three substituents chosen from the group consisting of halogen, nitro, cyano, $C_1$ to $C_6$ alkyl, $C_1$ to $C_6$ haloalkyl, $C_1$ to $C_6$ alkoxy and $C_1$ to $C_6$ alkylthio;

$R^3$ is chosen from the group consisting of: $C_1$ to $C_6$ alkyl; $C_1$ to $C_6$ fluoroalkyl; $C_2$ to $C_6$ alkenyl; $C_2$ to $C_6$ alkynyl; and phenyl; and n is an integer chosen from 2 to 5.

When in the compound of formula I $R^1$ is chosen from acyl the nature of the acyl group is not narrowly critical. Although not intending to be bound by theory, it is believed that when $R^1$ is acyl the acyl group is removed in the plant by hydrolysis to give the corresponding compound of formula I in which $R^1$ is hydrogen. Suitable acyl groups include: alkanoyl, for example $C_2$ to $C_6$ alkanoyl; aroyl, for example benzoyl and substituted benzoyl wherein the benzene ring is substituted with from one to three substituents chosen from the group consisting of halogen, nitro, cyano, $C_1$ to $C_6$ alkyl, $C_1$ to $C_6$ haloalkyl, $C_1$ to $C_6$ alkoxy and $C_1$ to $C_6$ alkylthio; and heteroaroyl, for example 2-furoyl, 3-furoyl, 2-thenoyl and 3-thenoyl.

When in the compound of formula I $R^1$ is chosen from an inorganic or organic cation the nature of the cation is not narrowly critical. Although not intending to be bound by theory, it is believed that when $R^1$ is a cation the cation is removed in the plant to give a compound of formula I wherein $R^1$ is hydrogen. Suitable inorganic cations include the alkali and alkaline earth metal ions, heavy metal ions including the transition metal ions, and the ammonium ion. Suitable organic cations include the cation $R^4R^5R^6R^7N^\oplus$ wherein $R^4$, $R^5$, $R^6$ and $R^7$ are independently chosen from the group consisting of: hydrogen; $C_1$ to $C_{10}$ alkyl; substituted $C_1$ to $C_{10}$ alkyl wherein the alkyl group is substituted with a substituent chosen from the group consisting of hydroxy, halogen and $C_1$ to $C_6$ alkoxy; phenyl; benzyl; and the groups substituted phenyl and substituted benzyl wherein the benzene ring is substituted with from one to three substituents chosen from the group consisting of halogen, nitro, cyano, $C_1$ to $C_6$ alkyl, $C_1$ to $C_6$ haloalkyl, $C_1$ to $C_6$ alkoxy and $C_1$ to $C_6$ alkylthio.

It should be recognized that when $R^1$ is hydrogen the compounds of the invention may exist in any one of three tautomeric forms as shown below:

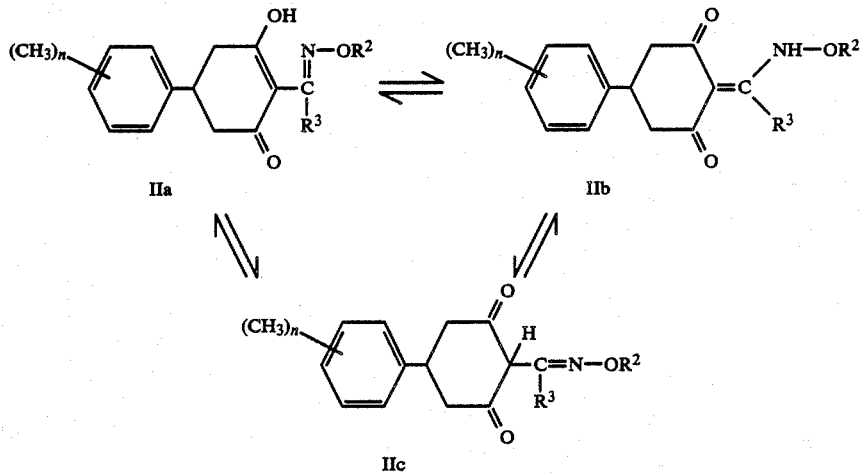

Suitable $R^1$ include hydrogen, $C_1$ to $C_6$ alkyl, $C_2$ to $C_6$ alkenyl, $C_2$ to $C_6$ alkynyl, $C_2$ to $C_6$ alkanoyl, $C_1$ to $C_6$ alkyl substituted with $C_1$ to $C_6$ alkoxy, $C_1$ to $C_6$ alkylthio, phenyl or substituted phenyl wherein the benzene ring is substituted with from one to three substituents chosen from the group consisting of halogen, nitro, cyano, $C_1$ to $C_6$ alkyl, $C_1$ to $C_6$ haloalkyl, $C_1$ to $C_6$ alkoxy and $C_1$ to $C_6$ alkylthio, benzoyl or substituted benzoyl wherein the benzene ring is substituted with from one to three substituents chosen from the group consisting of halogen, nitro, cyano, $C_1$ to $C_6$ alkyl, $C_1$ to $C_6$ haloalkyl, $C_1$ to $C_6$ alkoxy and $C_1$ to $C_6$ alkylthio, $C_1$ to $C_6$ (alkyl)sulfonyl and benzenesulfonyl or substituted benzenesulfonyl wherein the benzene ring is substituted with from one to three substituents chosen from the group consisting of halogen, nitro, cyano, $C_1$ to $C_6$ alkyl, $C_1$ to $C_6$ haloalkyl, $C_1$ to $C_6$ alkoxy and $C_1$ to $C_6$ alkylthio, and the group M wherein M is an alkali metal ion.

Suitable $R^2$ include $C_1$ to $C_6$ alkyl, $C_1$ to $C_6$ haloalkyl, $C_2$ to $C_6$ alkenyl, $C_2$ to $C_6$ alkynyl and $C_1$ to $C_6$ alkyl substituted with $C_1$ to $C_6$ alkoxy, $C_1$ to $C_6$ alkylthio, phenyl or substituted phenyl wherein the benzene ring is substituted with from one to three substituents chosen from the group consisting of halogen, nitro, cyano, $C_1$ to $C_6$ alkyl, $C_1$ to $C_6$ haloalkyl, $C_1$ to $C_6$ alkoxy and $C_1$ to $C_6$ alkylthio.

Suitable $R^3$ include $C_1$ to $C_6$ alkyl, $C_2$ to $C_6$ alkenyl and $C_2$ to $C_6$ alkynyl.

Preferred $R^1$ include: hydrogen; $C_2$ to $C_6$ alkanoyl; benzoyl and substituted benzoyl wherein the benzene ring is substituted with from 1 to 3 substituents selected from the group consisting of halogen, nitro, $C_1$ to $C_6$ alkyl and $C_1$ to $C_6$ alkoxy; and an inorganic or organic cation selected from the alkali metal ions, the alkaline earth metal ions, transition metal ions and the ammonium ion $R^4R^5R^6R^7N^{\oplus}$ wherein $R^4$, $R^5$, $R^6$ and $R^7$ are independently selected from the group consisting of hydrogen, $C_1$ to $C_{10}$ alkyl and substituted $C_1$ to $C_{10}$ alkyl wherein the alkyl group is substituted with a substituent selected from the group consisting of hydroxy and $C_1$ to $C_6$ alkoxy.

More preferred $R^1$ include hydrogen, acetyl, tertiary-butyryl, benzoyl, halobenzoyl, methylbenzoyl, methoxybenzoyl, nitrobenzoyl, trimethylbenzoyl, dinitrobenzoyl, the cations of the alkali metals sodium and potassium; the cations of the alkaline earth metals magnesium, calcium and barium, the cations of the transition metals manganese, copper, zinc, iron, nickel, cobalt and silver, the ammonium ion, and the tri- and tetraalkyl ammonium ions wherein alkyl is selected from $C_1$ to $C_6$ alkyl and $C_1$ to $C_6$ hydroxyalkyl.

Even more preferred $R^1$ include hydrogen, benzoyl, sodium and potassium.

Preferred $R^2$ include: $C_1$ to $C_6$ alkyl; $C_2$ to $C_6$ alkenyl; $C_2$ to $C_6$ alkynyl; $C_1$ to $C_6$ haloalkyl; $C_2$ to $C_6$ haloalkenyl; $C_1$ to $C_6$ alkyl substituted with $C_1$ to $C_6$ alkoxy; $C_1$ to $C_6$ alkyl substituted with $C_1$ to $C_6$ alkylthio; and benzyl and substituted benzyl wherein the benzene ring is substituted with from one to three substituents selected from the group consisting of halogen, nitro and $C_1$ to $C_6$ alkyl.

More preferred $R^2$ include ethyl, n-propyl, n-butyl, allyl, propargyl, 2-fluoroethyl, 2-chloroallyl, methylthiomethyl, benzyl, halobenzyl, methylbenzyl and nitrobenzyl.

Even more preferred $R^2$ include ethyl, n-propyl and allyl.

Preferred $R^3$ include $C_1$ to $C_6$ alkyl. More preferred $R^3$ include methyl, ethyl and n-propyl. Even more preferred $R^3$ include ethyl and n-propyl.

Preferred n is an integer selected from 3 to 5.

Particularly preferred compounds of the invention include those compounds of formula I in which the benzene ring is substituted in at least the 2-, 4- and 6-positions with methyl groups.

Specific examples of the compounds of the invention include those compounds detailed in Table 1 below.

TABLE 1

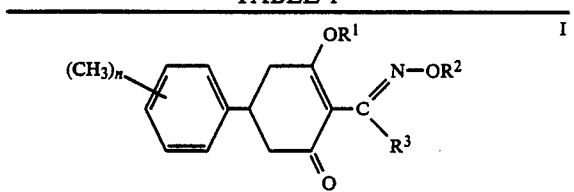

| Compound No | $(CH_3)_n$ | $R^1$ | $R^2$ | $R^3$ |
|---|---|---|---|---|
| 1 | 2,3-$(CH_3)_2$ | H | $C_2H_5$ | $C_2H_5$ |
| 2 | 2,4-$(CH_3)_2$ | H | $C_2H_5$ | $C_2H_5$ |
| 3 | 2,5-$(CH_3)_2$ | H | $C_2H_5$ | $C_2H_5$ |
| 4 | 2,6-$(CH_3)_2$ | H | $C_2H_5$ | $C_2H_5$ |
| 5 | 3,4-$(CH_3)_2$ | H | $C_2H_5$ | $C_2H_5$ |
| 6 | 3,5-$(CH_3)_2$ | H | $C_2H_5$ | $C_2H_5$ |
| 7 | 2,4,6-$(CH_3)_3$ | H | $C_2H_5$ | $C_2H_5$ |
| 8 | 2,4,5-$(CH_3)_3$ | H | $C_2H_5$ | $C_2H_5$ |
| 9 | 2,3,5,6-$(CH_3)_4$ | H | $C_2H_5$ | $C_2H_5$ |
| 10 | 2,3,4,6-$(CH_3)_4$ | H | $C_2H_5$ | $C_2H_5$ |
| 11 | 3,4-$(CH_3)_2$ | $COC_6H_5$ | $C_2H_5$ | $C_2H_5$ |
| 12 | 3,4-$(CH_3)_2$ | $COCH_3$ | $C_2H_5$ | $C_2H_5$ |
| 13 | 2,5-$(CH_3)_2$ | $COC_6H_5$ | $C_2H_5$ | $C_2H_5$ |
| 14 | 2,3-$(CH_3)_2$ | $COC_6H_5$ | $C_2H_5$ | $C_2H_5$ |
| 15 | 2,4,6-$(CH_3)_3$ | $COC_6H_5$ | $C_2H_5$ | $C_2H_5$ |
| 16 | 2,4,6-$(CH_3)_3$ | H | $CH_2CH=CH_2$ | $n$-$C_3H_7$ |
| 17 | 2,4,6-$(CH_3)_3$ | H | $CH_2CH=CH_2$ | $C_2H_5$ |
| 18 | 2,4,6-$(CH_3)_3$ | H | $C_2H_5$ | $n$-$C_3H_7$ |
| 19 | 2,4,6-$(CH_3)_3$ | H | $C_2H_5$ | $CH_3$ |
| 20 | 2,4,6-$(CH_3)_3$ | H | $n$-$C_3H_7$ | $C_2H_5$ |
| 21 | 2,4,6-$(CH_3)_3$ | H | $n$-$C_4H_9$ | $C_2H_5$ |
| 22 | 2,4,6-$(CH_3)_3$ | H | a | $C_2H_5$ |
| 23 | 2,4,6-$(CH_3)_3$ | H | b | $C_2H_5$ |
| 24 | 2,4,6-$(CH_3)_3$ | H | $CH_2C\equiv CH$ | $C_2H_5$ |
| 25 | 2,4,6-$(CH_3)_3$ | H | $CH_2CH_2F$ | $C_2H_5$ |
| 26 | 2,4,6-$(CH_3)_3$ | H | $CH_2C(Cl)=CH_2$ | $C_2H_5$ |
| 27 | 2,4,6-$(CH_3)_3$ | H | $CH_2C_6H_5$ | $C_2H_5$ |
| 28 | 2,4,6-$(CH_3)_3$ | H | c | $C_2H_5$ |
| 29 | 2,4,6-$(CH_3)_3$ | H | d | $C_2H_5$ |
| 30 | 2,4,6-$(CH_3)_3$ | H | e | $C_2H_5$ |
| 31 | 2,4,6-$(CH_3)_3$ | H | f | $C_2H_5$ |
| 32 | 2,4,6-$(CH_3)_3$ | H | g | $C_2H_5$ |
| 33 | 2,4,6-$(CH_3)_3$ | H | h | $C_2H_5$ |
| 34 | 2,4,6-$(CH_3)_3$ | H | i | $C_2H_5$ |
| 35 | 2,4,6-$(CH_3)_3$ | H | $n$-$C_4H_9$ | $n$-$C_3H_7$ |
| 36 | 2,4,6-$(CH_3)_3$ | H | a | $n$-$C_3H_7$ |
| 37 | 2,4,6-$(CH_3)_3$ | H | b | $n$-$C_3H_7$ |
| 38 | 2,4,6-$(CH_3)_3$ | H | $CH_2C\equiv CH$ | $n$-$C_3H_7$ |
| 39 | 2,4,6-$(CH_3)_3$ | H | $CH_2CH_2F$ | $n$-$C_3H_7$ |
| 40 | 2,4,6-$(CH_3)_3$ | H | $CH_2C(Cl)=CH_2$ | $n$-$C_3H_7$ |
| 41 | 2,4,6-$(CH_3)_3$ | H | c | $n$-$C_3H_7$ |
| 42 | 2,4,6-$(CH_3)_3$ | H | d | $n$-$C_3H_7$ |
| 43 | 2,4,6-$(CH_3)_3$ | $Na^\oplus$ | $C_2H_5$ | $C_2H_5$ |
| 44 | 2,4,6-$(CH_3)_3$ | j | $C_2H_5$ | $C_2H_5$ |
| 45 | 2,4,6-$(CH_3)_3$ | k | $C_2H_5$ | $C_2H_5$ |
| 46 | 2,4,6-$(CH_3)_3$ | l | $C_2H_5$ | $C_2H_5$ |
| 47 | 2,4,6-$(CH_3)_3$ | $Na^\oplus$ | $CH_2CH=CH_2$ | $C_2H_5$ |
| 48 | 2,4,6-$(CH_3)_3$ | $COC_6H_5$ | $CH_2CH=CH_2$ | $C_2H_5$ |
| 49 | 2,4,6-$(CH_3)_3$ | $COC_6H_5$ | $CH_2C\equiv CH$ | $C_2H_5$ |
| 50 | 2,4,6-$(CH_3)_3$ | $COC_6H_5$ | $C_2H_5$ | $n$-$C_3H_7$ |
| 51 | 2,4,6-$(CH_3)_3$ | $COC_6H_5$ | $CH_2CH=CH_2$ | $n$-$C_3H_7$ |
| 52 | 2,3,4-$(CH_3)_3$ | H | $C_2H_5$ | $C_2H_5$ |
| 53 | 2,3,5-$(CH_3)_3$ | H | $C_2H_5$ | $C_2H_5$ |
| 54 | 3,4,5-$(CH_3)_3$ | H | $C_2H_5$ | $C_2H_5$ |
| 55 | 2,3,4,6-$(CH_3)_4$ | H | $C_2H_5$ | $n$-$C_3H_7$ |
| 56 | 2,3,4,6-$(CH_3)_4$ | H | $CH_2CH=CH_2$ | $C_2H_5$ |
| 57 | 2,3,4,6-$(CH_3)_4$ | H | $CH_2CH=CH_2$ | $n$-$C_3H_7$ |
| 58 | 2,3,4,6-$(CH_3)_4$ | $COC_6H_5$ | $C_2H_5$ | $C_2H_5$ |
| 59 | 2,3,4,5-$(CH_3)_4$ | $Na^\oplus$ | $C_2H_5$ | $C_2H_5$ |
| 60 | 2,3,4,5,6-$(CH_3)_5$ | H | $C_2H_5$ | $C_2H_5$ |
| 61 | 2,3,4,5,6-$(CH_3)_5$ | H | $CH_2CH=CH_2$ | $C_2H_5$ |
| 62 | 2,3,4,5,6-$(CH_3)_5$ | H | $C_2H_5$ | $n$-$C_3H_7$ |
| 63 | 2,3,4,5,6-$(CH_3)_5$ | H | $CH_2CH=CH_2$ | $n$-$C_3H_7$ |
| 64 | 2,3,4,5-$(CH_3)_4$ | H | $C_2H_5$ | $C_2H_5$ |
| 65 | 3,4-$(CH_3)_2$ | H | $n$-$C_3H_7$ | $C_2H_5$ |
| 66 | 3,4-$(CH_3)_2$ | H | $CH_2CH=CH_2$ | $C_2H_5$ |
| 67 | 3,4-$(CH_3)_2$ | H | $C_2H_5$ | $n$-$C_3H_7$ |
| 68 | 3,4-$(CH_3)_2$ | H | $n$-$C_3H_7$ | $n$-$C_3H_7$ |
| 69 | 3,4-$(CH_3)_2$ | H | $CH_2CH=CH_2$ | $n$-$C_3H_7$ |
| 70 | 2,3,4,5,6-$(CH_3)_5$ | H | $C_2H_5$ | $CH_3$ |
| 71 | 2,3,6-$(CH_3)_3$ | H | $C_2H_5$ | $C_2H_5$ |
| 72 | 2,3,4,5,6-$(CH_3)_5$ | $Na^\oplus$ | $C_2H_5$ | $n$-$C_3H_7$ |
| 73 | 2,3,4,5,6-$(CH_3)_5$ | $COC_6H_5$ | $C_2H_5$ | $n$-$C_3H_7$ |
| 74 | 2,3,4,6-$(CH_3)_4$ | H | $CH_2CH_2F$ | $n$-$C_3H_7$ |
| 75 | 2,3,4,5,6-$(CH_3)_5$ | H | $CH_2CH_2F$ | $n$-$C_3H_7$ |
| 76 | 2,3,4,5,6-$(CH_3)_5$ | H | $CH_2CH_2F$ | $C_2H_5$ |
| 77 | 2,3,4,5,6-$(CH_3)_5$ | H | $CH_3$ | $n$-$C_3H_7$ |
| 78 | 2,3,4,5,6-$(CH_3)_5$ | $Na^\oplus$ | $C_2H_5$ | $C_2H_5$ |
| 79 | 2,3,4,5,6-$(CH_3)_5$ | H | $n$-$C_3H_7$ | $n$-$C_3H_7$ |
| 80 | 2,3,4,5,6-$(CH_3)_5$ | H | $CH_3$ | $C_2H_5$ |
| 81 | 2,3,4,5,6-$(CH_3)_5$ | $COC_6H_5$ | $C_2H_5$ | $C_2H_5$ |
| 82 | 2,3,4,5,6-$(CH_3)_5$ | H | $CH_2C(Cl)=CH_2$ | $n$-$C_3H_7$ |
| 83 | 2,3,4,5,6-$(CH_3)_5$ | H | a | $C_2H_5$ |
| 84 | 2,3,4,5,6-$(CH_3)_5$ | ½$Cu^{2+}$ | $C_2H_5$ | $n$-$C_3H_7$ |
| 85 | 2,3,4,5,6-$(CH_3)_5$ | ½$Ni^{2+}$ | $C_2H_5$ | $n$-$C_3H_7$ |
| 86 | 2,3,4,5,6-$(CH_3)_5$ | H | $CH_2SCH_3$ | $C_2H_5$ |
| 87 | 2,5-$(CH_3)_2$ | H | $C_2H_5$ | $C_6H_5$ |
| 88 | 2,4,6-$(CH_3)_3$ | $^\oplus N(n$-$C_4H_9)_4$ | $C_2H_5$ | $C_2H_5$ |
| 89 | 2,4,6-$(CH_3)_3$ | m | $C_2H_5$ | $C_2H_5$ |
| 90 | 2,4,6-$(CH_3)_3$ | n | $C_2H_5$ | $C_2H_5$ |
| 91 | 2,4,6-$(CH_3)_3$ | o | $C_2H_5$ | $C_2H_5$ |
| 92 | 2,4,6-$(CH_3)_3$ | p | $C_2H_5$ | $C_2H_5$ |
| 93 | 2,4,6-$(CH_3)_3$ | $CH_3CO$ | $C_2H_5$ | $C_2H_5$ |
| 94 | 2,4,6-$(CH_3)_3$ | q | $C_2H_5$ | $C_2H_5$ |
| 95 | 2,4,6-$(CH_3)_3$ | r | $C_2H_5$ | $C_2H_5$ |

Footnotes to Table 1
a trans - $CH_2CH=CHCH_3$
b $CH_2CH_2CH=CH_2$
c $CH_2C_6H_4Cl$—4
d $CH_2C_6H_4Br$—4
e $CH_2C_6H_4F$—4
f $CH_2C_6H_4CH_3$—4
g $CH_2C_6H_4NO_2$—4
h $CH_2C_6H_4Cl$—3
i $CH_2C_6H_3Cl_2$—2,4
j $COC_6H_4NO_2$—4
k $COC_6H_4NO_2$—3
l $COC_6H_3(NO_2)_2$—3,5
m $COC_6H_4CH_3$—4
n $COC_6H_2(CH_3)_3$—2,4,6
o $COC_6H_4OCH_3$—4
p $COC_6H_4Cl$—4
q $COC(CH_3)_3$
r $CH_2COOCH_2CH_3$ The compounds of the invention may be prepared by a variety of methods and in a further aspect the the invention provides methods for the preparation of compounds of formula I.

Conveniently the preparation of the compounds of the invention can be considered in three or four parts.

Part A involves the formation of a 5-(substituted phenyl)cyclohexane-1,3-dione of formula IX. This reaction may be carried out in a two step process by condensing a benzaldehyde derivative of formula V with acetone to form a ketone of formula VI, which is in turn condensed with a malonic acid ester of formula VII to give a 5-(substituted phenyl)cyclohexane-1,3-dione of formula IX, either with or without the isolation of the intermediate of formula VIII.

Alternatively, this preparation may be carried out in a two step process by condensing a benzaldehyde derivative of formula V with a malonic acid ester of formula VII to give a benzylidenemalonate derivative of formula X which is in turn condensed with an acetoacetic acid ester of formula XI to give a 5-(substituted phenyl)- cyclohexane-1,3-dione of formula IX, either with or without isolation of the intermediate of formula XII.

In a further alternative process this preparation may be carried out by condensing a cinnamate of formula XXI with an acetoacetic acid ester of formula XI to give a 5-(substituted phenyl)cyclohexane-1,3-dione of formula IX, either with or without isolation of the intermediate of formula VIII.

The above reaction sequences are set out in SCHEME A parts (i), (ii) and (iii) respectively below, wherein R represents a $C_1$ to $C_6$ alkyl group.

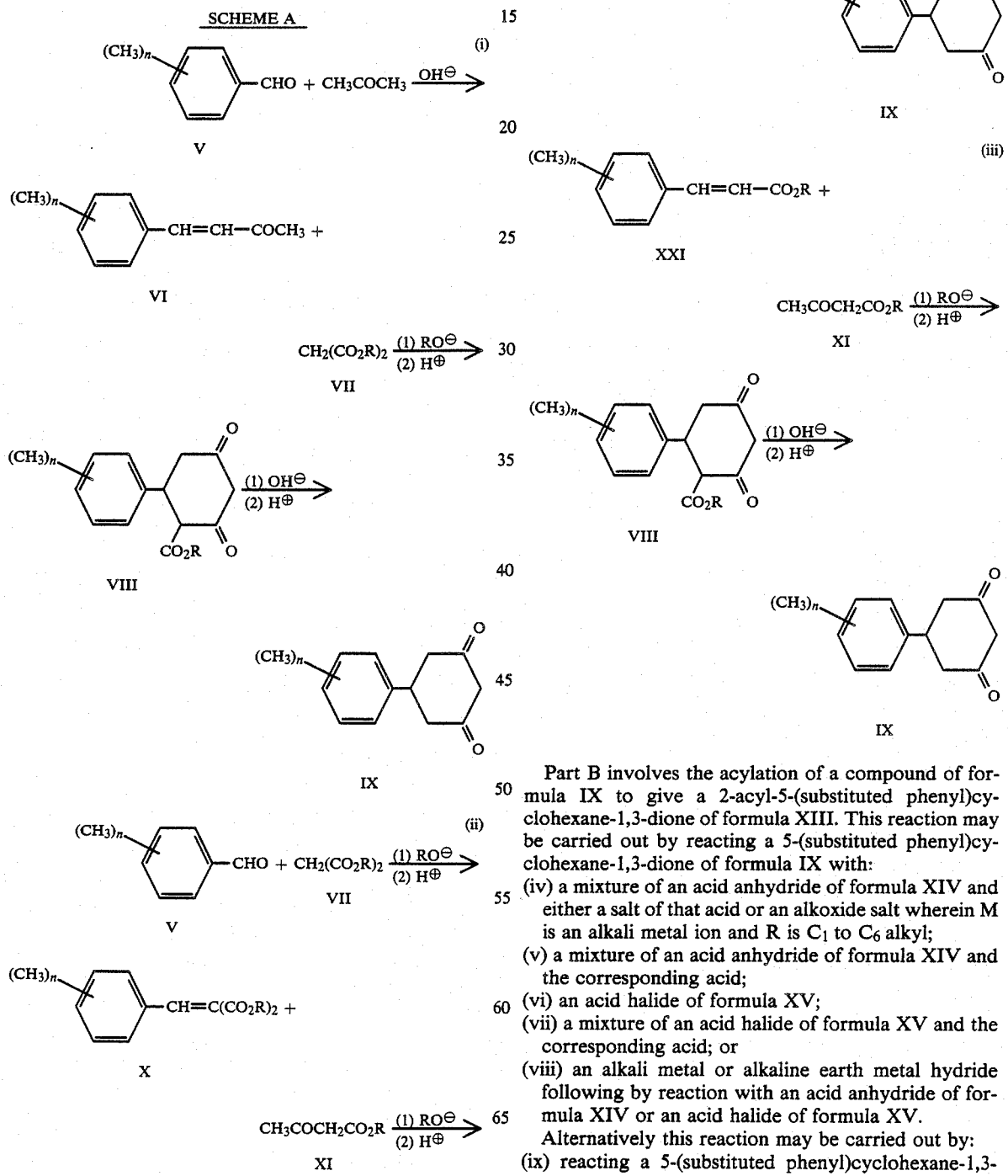

Part B involves the acylation of a compound of formula IX to give a 2-acyl-5-(substituted phenyl)cyclohexane-1,3-dione of formula XIII. This reaction may be carried out by reacting a 5-(substituted phenyl)cyclohexane-1,3-dione of formula IX with:

(iv) a mixture of an acid anhydride of formula XIV and either a salt of that acid or an alkoxide salt wherein M is an alkali metal ion and R is $C_1$ to $C_6$ alkyl;

(v) a mixture of an acid anhydride of formula XIV and the corresponding acid;

(vi) an acid halide of formula XV;

(vii) a mixture of an acid halide of formula XV and the corresponding acid; or (viii) an alkali metal or alkaline earth metal hydride following by reaction with an acid anhydride of formula XIV or an acid halide of formula XV.

Alternatively this reaction may be carried out by:

(ix) reacting a 5-(substituted phenyl)cyclohexane-1,3-dione of formula IX with an acid halide of formula XV in the presence of pyridine to give an intermediate O-acyl derivative of formula XVI; and then:

(x) reacting the intermediate of formula XVI with a Lewis acid catalyst;

(xi) reacting the intermediate of formula XVI with the corresponding acid of the acid halide of formula XV; or (xii) reacting the intermediate of formula XVI with imidazole.

Each of these reactions is outlined in SCHEME B below wherein hal represents halogen.

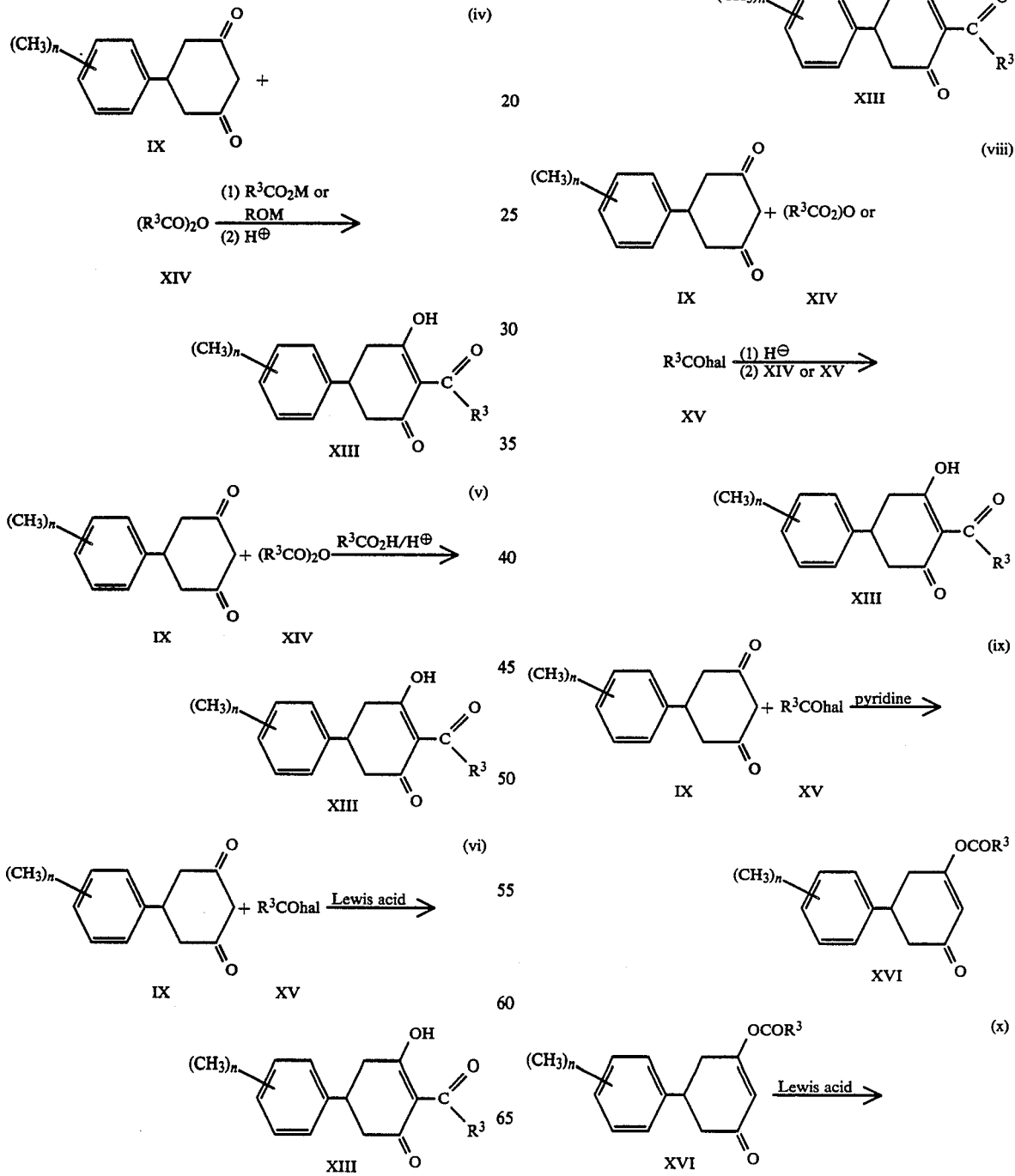

-continued
SCHEME B

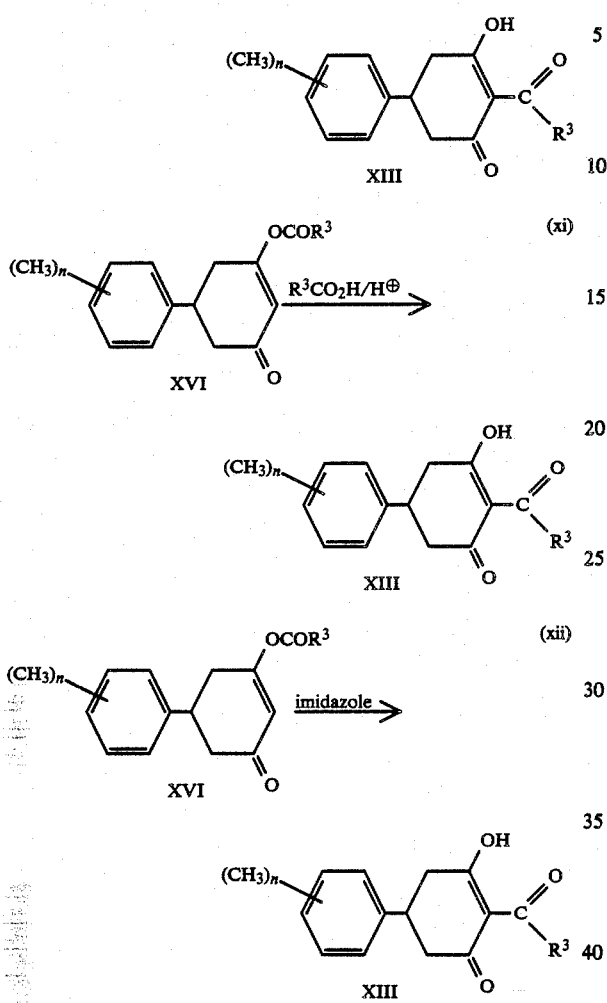

SCHEME C

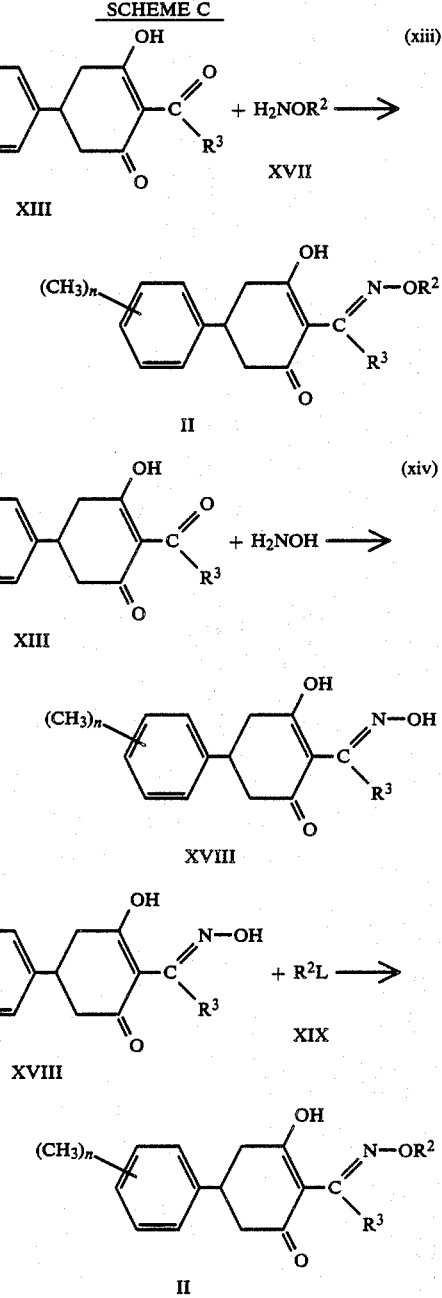

Part C involves the formation of a compound of the invention of formula I wherein $R^1$ is hydrogen, that is a compound of formula II. This reaction may be carried out either:

(xiii) by reacting a compound of formula XIII with an alkoxyamine derivative of formula XVII to give a compound of formula II; or (xiv) by reacting a compound of formula XIII with hydroxylamine to give an intermediate oxime derivative of formula XVIII and reacting the oxime derivative of formula XVIII with an alkylating agent of formula XIX to give a compound of formula II.

These reaction sequences are set out in SCHEME C below wherein L is a good leaving group such as, for example, chloride, bromide, iodide, sulfate, nitrate, methyl sulfate, ethyl sulfate, tetrafluoroborate, hexafluorophosphate, hexafluoroantimonate, methanesulfonate, fluorosulfonate, fluoromethanesulfonate and trifluoromethanesulfonate.

Compounds of the invention of formula I wherein $R^1$ is an acyl or a sulfonyl group may be prepared from compounds of the invention of formula I wherein $R^1$ is hydrogen, that is, compounds of formula II, by etherification, acylation, or sulfonylation as required. This reaction is outlined in SCHEME D below.

SCHEME D

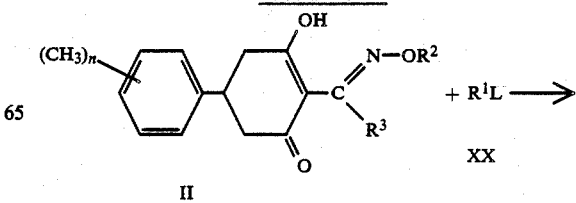

-continued
SCHEME D

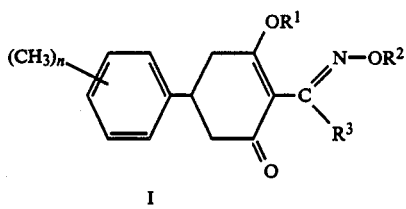

I

Compounds of the invention of formula I wherein $R^1$ is an inorganic or organic cation may be prepared from the compounds of the invention of formula I wherein $R^1$ is hydrogen, that is, compounds of formula II, by reacting said compounds of formula II with an inorganic or organic salt. For example, the compounds of formula I werein $R^1$ is an alkalki metal ion may be prepared by reacting the appropriate compound of formula II with the appropriate alkali metal hydroxide or alkoxylate. The compounds of formula I wherein $R^1$ is a transition metal ion or an organic cation may similarly be prepared by reacting the appropriate compound of formula II with an appropriate transition metal salt or organic base. Alternatively, the compounds of formula I wherein $R^1$ is a transition metal ion or an organic cation may be prepared by reacting the appropriate compound of formula I wherein $R^1$ is an alkali metal ion with an appropriate transition metal salt or organic salt.

Accordingly, in a further aspect the invention provides a process for the preparation of a compound of formula I, wherein $R^1$, $R^2$ and $R^3$ are as hereinbefore defined, which process comprises:

(a) reacting a benzaldehyde derivative of formula V with acetone to give a ketone derivative of formula VI and reacting the ketone derivative of formula VI with a malonic acid ester of formula VII, wherein R is $C_1$ to $C_6$ alkyl, to give a 5-(substituted phenyl)cyclohexane-1,3-dione derivative of formula IX; or reacting a benzaldehyde derivative of formula V with a malonic acid ester of formula VII to give a benzylidenemalonate derivative of formula X and reacting the benzylidenemalonate derivative of formula X with an acetoacetic acid ester of formula XI, wherein R is $C_1$ to $C_6$ alkyl, to give a 5-(substituted phenyl)cyclohexane-1,3-dione derivative of formula IX; or reacting a cinnamate of formula XXI, wherein R is $C_1$ to $C_6$ alkyl, with an acetoacetic acid ester of formula XI, wherein R is $C_1$ to $C_6$ alkyl, to give a 5-(substituted phenyl)cyclohexane-1,3-dione derivative of formula IX;

(b) acylating the 5-(substituted phenyl)cyclohexane-1,3-dione derivative of formula IX with an acid anhydride of formula XIV or an acid halide of formula XV to give a 2-acyl-5-(substituted phenyl)cyclohexane-1,3-dione derivative of formula XIII;

(c) reacting the 2-acyl-5-(substituted phenyl)cyclohexane-1,3-dione derivative of formula XIII with an alkoxyamine derivative of formula XVII to give a compound of the invention of formula II or reacting the 2-acyl-5-(substituted phenyl)cyclohexane-1,3-dione derivative of formula XIII with hydroxylamine and alkylating the oxime intermediate of formula XVIII with an alkylating agent of formula XIX, wherein L is a good leaving group, to give a compound of the invention of formula II; and optionally (d) reacting the compound of the invention of formula II with a compound of formula XX, wherein L is a good leaving group, or reacting the compound of the invention of formula II with an inorganic or organic base or salt, to give a compound of the invention of formula I.

Certain of the intermediate compounds of formulae VI, VIII, IX, X, XII, XXI, XIII, XVI and XVIII are novel compounds and therefore as a further embodiment the invention provides novel compounds of formulae VI, VIII, IX, X, XII, XXI, XIII, XVI and XVIII, wherein the substituents are as hereinbefore defined, and processes for the preparation thereof.

The compounds of formula I are active as herbicides against monocotyledonous weeds, wild grasses, and in particular are selectively active against difficultly controllable wild grasses in crops of cultivated plants. The compounds of the invention are especially useful in the control of wild grasses such as wild oats and rye grass in crops of cultivated monocotyledonous plants such as wheat, barley and other varieties of cereals.

Accordingly, in yet a further aspect the invention provides a process for controlling monocotyledonous weeds in cultivated crops, especially wild grasses in cereal crops such as wheat and barley, which process comprises applying to the crop, or to the growth medium of the crop, a compound of formula I, as hereinbefore defined, in an amount sufficient to severely damage or kill the weeds but insufficient to damage the crop substantially.

As hereinbefore indicated, certain cyclohexane-1,3-dione derivatives, such as those disclosed in Australian Pat. No. 464,655 and Australian Patent Application No. 35,314/78 and numerous other patents and patent applications, are known to be general grass herbicides which show no useful cereal selectivity. Moreover, it is known from the teaching of Iwataki and Hirono ("Advances in Pesticides Science-Part 2", pp 235–243, Pergamon Press, 1979) that some cereal selectivity is observed in such cyclohexane-1,3-dione derivatives when a phenyl group substituted in the para-position is introduced into the 5-position of the cyclohexane ring but that "The selectivity was found only in the case of para-substituents at the phenyl nucleus and that the effect was not found in the case of di- or tri-substitution". Therefore, it is completely unexpected to find that the cyclohexane-1,3-dione derivatives of the present invention, which have, located in the 5-position of the cyclohexane ring, a phenyl group which is in turn substituted with from two to five methyl groups, are cereal selective herbicides which effectively control monocotyledonous weeds such as wild oats and rye grass in crops of sensitive, cultivated monocotyledonous plants such as wheat and barley. It is even more surprising to find that those cyclohexane-1,3-dione derivatives of the present invention which have, located in the 5-position of the cyclohexane ring, a phenyl group which is in turn substituted with methyl groups in at least the 2-, 4- and 6-positions, are highly active against monocotyledonous weeds such as wild oats and rye grass at very low rates of application and at the same time are very safe on wheat, a sensitive, cultivated monocytyledonous plant.

The compounds of formula I may be applied directly to the plant (post-emergence application) or to the soil before the emergence of the plant (pre-emergence application). However, the compounds are, in general, more effective when applied to the plant post-emergence.

The compounds of formula I may be used on their own to inhibit the growth of, severely damage, or kill plants but are preferably used in the form of a composition comprising a compound of the invention in admixture with a carrier. Therefore, in yet a further aspect the invention provides plant growth inhibiting, plant damaging, or plant killing compositions comprising a compound of formula I as hereinbefore defined and an inert carrier therefor.

The compositions of the present invention may be in the form of solids, liquids or pastes. The compositions include both dilute compositions which are ready for immediate use and concentrated compositions which may require dilution before use. Therefore, the concentration of the active ingredient in the compositions of the present invention will vary depending on the type of formulation and whether the composition is ready for use such as, for example, a dust formulation or an aqueous emulsion or whether the composition is a concentrate such as, for example, an emulsifiable concentrate or a wettable powder, which is suitable for dilution before use. In general the compositions of the present invention comprise from 0.01% to 99% by weight of active ingredient.

The solid compositions may be in the form of powders, dusts, pellets, grains, and granules wherein the active ingredient is mixed with a solid diluent. Powders and dusts may be prepared by mixing or grinding the active ingredient with a solid carrier to give a finely divided composition. Granules, grains and pellets may be prepared by bonding the active ingredient to a solid carrier, for example, by coating or impregnating the preformed granular solid carrier with the active ingredient or by agglomeration techniques.

Examples of solid carriers include: mineral earths and clays such as, for example, kaoline, bentonite, kieselguhr, Fuller's earth, Attaclay, diatomaceous earth, bole, loess, talc, chalk, dolomite, limestone, lime, calcium carbonate, powdered magnesia, magnesium oxide, magnesium sulfate, gypsum, calcium sulfate, pyrophyllite, silicic acid, silicates and silica gels; fertilizers such as, for example, ammonium sulfate, ammonium phosphate, ammonium nitrate and urea; natural products of vegetable origin such as, for example, grain meals and flours, bark meals, wood meals, nutshell meals and cellulosic powders; and synthetic polymeric materials such as, for example, ground or powdered plastics and resins.

Alternatively, the solid compositions may be in the form of dispersible or wettable dusts, powders, granules or grains wherein the active ingredient and the solid carrier are combined with one or more surface active agents which act as wetting, emulsifying and/or dispersing agents to facilitate the dispersion of the active ingredient in liquid.

Examples of surface active agents include those of the cationic, anionic and non-ionic type. Cationic surface active agents include quaternary ammonium compounds, for example, the long chain alkylammonium salts such as cetyltrimethylammonium bromide. Anionic surface active agents include: soaps or the alkali metal, alkaline earth metal and ammonium salts of fatty acids; the alkali metal, alkaline earth metal and ammonium salts of ligninsulfonic acid; the alkali metal, alkaline earth metal and ammonium salts of arylsulfonic acids including the salts of naphthalenesulfonic acids such as butylnapththalenesulfonic acid, the di- and tri-isopropylnaphthalenesulfonic acids, the salts of the condensation products of sulfonated naphthalene and naphthalene derivatives with formaldehyde, the salts of the condensation products of sulfonated naphthalene and naphthalene derivatives with phenol and formaldehyde, and the salts of alkylarylbenzenesulfonic acids such as dodecylbenzenesulfonic acid; the alkali metal, alkaline earth metal and ammonium salts of the long chain mono esters of sulfuric acid or alkylsulfates such as laurylsulfate and the mono esters of sulfuric acid with fatty alcohol glycol ethers. Nonionic surface active agents include: the condensation products of ethylene oxide with fatty acohols such as oleyl alcohol and cetyl alcohol; the condensation products of ethylene oxide with phenols and alkylphenols such as isooctylphenol, octylphenol and nonylphenol; the condensation products of ethylene oxide with castor oil; the partial esters derived from long chain fatty acids and hexitol anhydrides, for example sorbitan monolaurate, and their condensation products with ethylene oxide; ethylene oxide/propylene oxide block copolymers; lauryl alcohol polyglycol ether acetal; and the lecithins.

The liquid compositions may comprise a solution or dispersion of the active ingredient in a liquid carrier optionally containing one or more surface active agents which act as wetting, emulsifying and/or dispersing agents. Examples of liquid carriers include: water; mineral oil fractions such as, for example, kerosene, solvent naphtha, petroleum, coal tar oils and aromatic petroleum fractions; aliphatic, cycloaliphatic and aromatic hydrocarbons such as, for example, paraffin, cyclohexane, toluene, the xylenes, tetrahydronaphthalene and alkylated naphthalenes; alcohols such as, for example, methanol, ethanol, propanol, isopropanol, butanol, cyclohexanol and propylene glycol; ketones such as, for example, cyclohexanone and isophorone; and strongly polar organic solvents such as, for example, dimethylformamide, dimethylsulfoxide, N-methylpyrrolidone and sulfolane.

A preferred liquid composition comprises an aqueous suspension, dispersion or emulsion of the active ingredient which is suitable for application by spraying, atomixing or watering. Such aqueous compositions are generally prepared by mixing concentrated compositions with water. Suitable concentrated compositions include emulsion concentrates, pastes, oil dispersions, aqueous suspensions and wettable powders. The concentrates are usually required to withstand storage for prolonged periods and after such storage to be capable of dilution with water to form aqueous preparations which remain homogeneous for a sufficient time to enable them to be applied by conventional spray equipment. The concentrates conveniently contain from 20 to 99%, preferably 20 to 60%, by weight of active ingredient.

Emulsion or emulsifiable concentrates are conveniently prepared by dissolving the active ingredient in an organic solvent containing one or more surface active agents. Pastes may be prepared by blending the finely divided active ingredient with a finely divided solid carrier, one or more surface active agents and optionally an oil. Oil dispersions may be prepared by grinding together the active ingredient, a hydrocarbon oil, and one or more surface active agents. Aqueous suspension concentrates may conveniently be prepared by ball milling a mixture of the active ingredient, water, at least one surface active agent and preferably at least one suspending agent. Suitable suspending agents include: hydrophilic colloids such as, for example, poly(N-vinylpyrrolidone), sodium carboxymethylcellulose and the vegetable gums gum acacia and gum tragacanth; hydrated colloidal mineral silicates such as, for example, montmorillonite, beidellite, nontronite, hectorite, saponite, sauconite and bentonite; other cellulose derivatives; and poly(vinyl alcohol). Wettable powder concentrates may conveniently be prepared by blending together the active ingredient, one or more surface active agents, one or more solid carriers and optionally one or more suspending agents and grinding the mixture to give a powder having the required particle size.

The aqueous suspensions, dispersions or emulsions may be prepared from the concentrated compositions by mixing the concentrated compositions with water optionally containing surface active agents and/or oils.

It should be noted that the compounds of the invention of formula I wherein $R^1$ is hydrogen are acidic. Therefore, the compounds of formula I may be formulated and applied as the salts of organic or inorganic bases. In formulating and employing the compounds of formula I in the form of their salts either the salts per se, that is the compounds of formula I wherein $R^1$ is an inorganic or an organic cation, may be used in the formulation or the compounds of formula I wherein $R^1$ is hydrogen may be used in the formulation and the salts generated in situ by the use of the appropriate organic or inorganic base.

The mode of application of the compositions of the invention will depend to a large extent on the type of composition used and the facilities available for its application. Solid compositions may be applied by dusting or any other suitable means for broadcasting or spreading the solid. Liquid compositions may be applied by spraying, atomizing, watering, introduction into the irrigation water, or any other suitable means for broadcasting or spreading the liquid.

The rate of application of the compounds of the invention will depend on a number of factors including, for example, the compound chosen for use, the identity of the plants whose growth is to be inhibited the formulations selected for use and whether the compound is to be applied for foliage or root uptake. As a general guide, however, an application rate of from 0.005 to 20 kilograms per hectare is suitable while from 0.01 to 5.0 kilograms per hectare may be preferred.

The compositions of the invention may comprise, in addition to one or more compounds of the invention, one or more compounds not of the invention but which possess biological activity. For example, as hereinbefore indicated the compounds of the invention are in general substantially more effective against monocotyledonous plants or grass species than against dicotyledonous plants or broad-leaved species. As a result, in certain applications the herbicidal use of the compounds of the invention alone may not be sufficient to protect a crop. Accordingly in yet a still further embodiment the invention provides a herbicidal composition comprising a mixture of at least one herbicidal compound of formula I as hereinbefore defined with at least one other herbicide.

The other herbicide may be any herbicide not having the formula I. It will generally be a herbicide having a complementary action. For example, one preferred class is of mixtures comprising a herbicide active against broad-leaved weeds. A second preferred class is of mixtures comprising a contact herbicide.

Examples of useful complementary herbicides include:

A. benzo-2,1,3-thiadiazin-4-one-2,2-dioxides such as 3-isopropylbenzo-2,1,3-thiadiazin-4-one-2,2-dioxide (common name bentazon);

B. hormone herbicides and in particular the phenoxyalkanoic acids such as 4-chloro-2-methylphenoxy acetic acid (common name MCPA), 2-(2,4-dichlorophenoxy)propionic acid (common name dichlorprop), 2,4,5-trichlorophenoxyacetic acid (common name 2,4,5-T), 4-(4-chloro-2-methylphenoxy)butyric acid (common name MCPB), 2,4-dichlorophenoxyacetic acid (common name 2,4-D), 4-(2,4-dichlorophenoxy)butyric acid (common name 2,4-DB), 2-(4-chloro-2-methylphenoxy)propionic acid (common name mecoprop), and their derivatives (eg salts, esters, amides and the like);

C. 3-8 4-(4-halophenoxy)phenyl]-1,1-dialkylureas such as 3-[4-(4-chlorophenoxy)phenyl]-1,1-dimethylurea (common name chloroxuron);

D. dinitrophenols and their derivatives (eg acetates) such as 2-methyl-4,6-dinitrophenol (common name DNOC), 2-tertiarybutyl-4,6-dinitrophenol (common name dinoterb), 2-secondarybutyl-4,6-dinitrophenol (common name dinoseb) and its ester dinoseb acetate;

E. dinitroaniline herbicides such as N',N'-diethyl2,6-dinitro-4-trifluoromethyl-m-phenylenediamine (common name dinitramine), 2,6-dinitro-N,N-dipropyl-4-trifluoromethylaniline (common name trifluralin) and 4-methylsulfonyl-2,6-dinitro-N,N-dipropylaniline (common name nitralin);

F. phenylurea herbicides such as N'-(3,4-dichlorophenyl)-N,N-dimethylurea (common name diuron) and N,N-dimethyl-N'-[3-(trifluoromethyl)phenyl]urea (common name fluometuron);

G. phenylcarbamoyloxyphenylcarbamates such as 3-[(methoxycarbonyl)amino]phenyl (3-methylphenyl)-carbamate (common name phenmedipham) and 3-[(ethoxycarbonyl)amino]phenyl phenylcarbamate (common name desmedipham);

H. 2-phenylpyridazin-3-ones such as 5-amino-4-chloro-2-phenylpyridazin-3-one (common name pyrazon);

I. uracil herbicides such as 3-cyclohexyl-5,6-trimethyleneuracil (common name lenacil), 5-bromo-3-sec-butyl-6-methyluracil (common name bromacil) and 3-tert-buty-5-chloro-6-methyluracil (common name terbacil);

J. triazine herbicides such as 2-chloro-4-ethylamino-6-(iso-propylamino)-1,3,5-triazine (common name atrazine), 2-chloro-4,6-di(ethylamino)-1,3,5-triazine (common name simazine) and 2-azido-4-(iso-propylamino)-6-methylthio-1,3,5-triazine (common name aziproptryne);

K. 1-alkoxy-2-alkyl-3-phenylurea herbicides such as 3-(3,4-dichlorophenyl)-1-methoxy-1-methylurea (common name linuron), 3-(4-chlorophenyl)-1-methoxy-1-methylurea (common name monolinuron) and 3-(4-bromo-4-chlorophenyl)-1-methoxy-1-methylurea (common name chlorobromuron);

L. thiolcarbamate herbicides such as S-propyl dipropylthiocarbamate (common name verolate);

M. 1,2,4-triazin-5-one herbicides such as 4-amino-4,5-dihydro-3-methyl-6-phenyl-1,2,4-triazine-5-one (common name metamitron) and 4-amino-6-tert-butyl-4,5-dihydro-3-methylthio-1,3,4-triazin-5-one (common name metribuzin);

N. benzoic acid herbicides such as 2,3,6-trichlorobenzoic acid (common name 2,3,6-TBA), 3,6-dichloro-2-methoxybenzoic acid (common name dicamba) and 3-amino-2,5-dichlorobenzoic acid (common name chloramben).

O. anilide herbicides such as N-butoxymethyl-α-chloro-2',6'-diethylacetanilide (common name butachlor), the corresponding N-methoxy compound (common name alachlor), the corresponding N-iso-propyl compound (common name propachlor) and 3',4'-dichloropropionanilide (common name propanil);

P. dihalobenzonitrile herbicides such as 2,6-dichlorobenzonitrile (common name dichlorobenil), 3,5-dibromo-4-hydroxybenzonitrile (common name bromoxynil) and 3,5-diiodo-4-hydroxybenzonitrile (common name ioxynil).

Q. haloalkanoic herbicides such as 2,2-dichloropropionic acid (common name dalapon), trichloroacetic acid (common name TCA) and salts thereof;

R. diphenylether herbicides such as 4-nitrophenyl 2-nitro-4-trifluoromethylphenyl ether (common name fluorodifen), methyl 5-(2,4-dichlorophenoxy)-2-nitrobenzoate (common name bifenox), 2-nitro-5-(2-chloro-4-trifluoromethylphenoxy)benzoic acid and 2-chloro-4-trifluoromethylphenyl 3-ethoxy-4-nitrophenyl ether;

S. N-(heteroarylaminocarbonyl)benzenesulfonamides such as 2-chloro-N-[(4-methoxy-6-methyl-1,3,5-triazin-2-yl)aminocarbonyl]benzenesulfonamide (commonly known as DPX 4189); and T. miscellaneous herbicides including N,N-dimethyldiphenylacetamide (common name diphenamid), N-(1-naphthyl)phthalamic acid (common name naptalam) and 3-amino-1,2,4-triazole.

Examples of useful contact herbicides include:

U. bipyridylium herbicides such as those in which the active entity is the 1,1'-dimethyl-4,4'-dipyridylium ion (common name paraquat) and those in which the active entity is the 1,1'-ethylene-2,2'-dipyridylium ion (common name diquat);

V. organoarsenical herbicides such as monosodium methanearsonate (common name MSMA); and W. amino acid herbicides such as N-(phosphonomethyl)glycine (common name glyphosate) and its salts and esters.

The invention is now illustrated by, but in no way limited to, the following Examples.

EXAMPLE 1

2-[1-(Ethoxyimino)propyl]-3-hydroxy-5-mesitylcyclohex-2-en-1-one (7)

(i) An aqueous solution of 1% sodium hydroxide (29.5 ml) was added dropwise over a period of 5 minutes to a suspension of mesityladehyde (10.0 g; 68 mmole) in acetone (50 ml) and water (50 ml). The mixture was stirred at a temperature of 65° C. for a period of 1½ hours and then was extracted with dichloromethane (200 ml). The organic extract was washed several times with water, dried over anhydrous sodium sulfate, and the solvent was removed by evaporation under reduced pressure using a rotary evaporator. The product 1-(2,4,6-trimethylphenyl)but-1-en-3-one, a viscous oil, solidified on standing to give a white solid (11.5 g; 90%), mp 64° C. Proton magnetic resonance spectrum (CDCl$_3$; $\delta$ in ppm): 2.25 (12H, m); 6.30 (1H, d); 6.88 (2H, s); 7.64 (1H, d).

(ii) Diethyl malonate (10.1 g; 60 mmole) was added to a solution of sodium metal (1.4 g; 60 mmole) in anhydrous absolute ethanol (50 ml) and the mixture was heated to reflux temperature. A mixture of 1-(2,4,6-trimethylphenyl)but-1-en-3-one (11.4 g; 61 mmole) in anhydrous absolute ethanol (50 ml) was added over a period of 2 minutes and the mixture was heated under reflux for a period of 2 hours. An aqueous solution of sodium hydroxide (7.3 g; 180 mmole in 100 ml of water) was added and the mixture was heated under reflux for a further 4½ hours. The solution was poured into water (200 ml) and the aqueous mixture was extracted twice with ethyl acetate (100 ml). The aqueous phase was acidified with concentrated hydrochloric acid and warmed gently until the evolution of carbon dioxide ceased. The aqueous mixture was extracted with ethyl acetate, dried over anhydrous sodium sulfate, and the solvent was removed by evaporation under reduced pressure using a rotary evaporator. The product, 3-hydroxy-5-mesitylcyclohex-2-en-1-one, was obtained as a pale yellow solid (10.9 g; 77.4%), mp 165° C. Proton magnetic resonance spectrum (D$_6$-dimethylsulfoxide; $\delta$ in ppm): 2.0–4.1 (14H, m); 5.2 (1H, s); 6.8 (2H, s); 11.2 (1H, br.s.).

(iii) Propionic anhydride (15.0 ml) was added cautiously to freshly prepared sodium methoxide (0.47 g; 9 mmole). On completion of the reaction 3-hydroxy-5-mesitylcyclohex-2-en-1-one (5.0 g; 22 mmole) was added and the reaction mixture was heated under reflux at a temperature of 160° C. for a period of 2 hours. The excess propionic anhydride was removed by evaporation under reduced pressure using a rotary evaporator. Aqueous 30% sodium hydroxide solution (50 ml) was added to the residue and the mixture was heated under reflux for a period of 1 hour with vigorous stirring. After cooling the mixture was acidified with concentrated hydrochloric acid and the aqueous mixture was extracted with dichloromethane. The organic extracts were dried over anhydrous sodium sulfate and the solvent was removed by evaporation under reduced pressure using a rotary evaporator. The product, a brown oil, was purified by chromatography over silica gel (eluant dichloromethane) to give 3-hydroxy-5-mesityl-2-propionylcyclohex-2-en-1-one (3.17 g; 50.2%) as a pale yellow oil. Proton magnetic resonance spectrum (CDCl$_3$; $\delta$ in ppm): 1.60 (3H, t, J=8 Hz); 2.24 (3H, s); 2.37 (6H, s); 2.64–5.26 (7H, m), 6.84 (2H, m); 18.26 (1H, s).

(iv) Ethoxyamine hydrochloride (0.45 g) and then aqueous 1% sodium hydroxide (18.4 ml) were added to a solution of 3-hydroxy-5-mesityl-2-propionylcyclohex-2-en-1-one (1.2 g; 4.2 mmole) in anhydrous absolute ethanol (200 ml). The mixture was stirred at room temperature for a period of 4 hours and then the ethanol was removed by evaporation under reduced pressure using a rotary evaporator. The residue was treated with dichloromethane and the organic phase was washed twice with dilute aqueous hydrochloric acid and twice with water. The organic phase was dried over anhydrous sodium sulfate and the solvent was removed by evaporation under reduced pressure to give the product, 2-[1-(ethoxyimino)propyl]-3-hydroxy-5-mesitylcyclohex-2-en-1-one (1.25 g; 93%), as a pale yellow oil.

The product was characterized by proton nuclear magnetic resonance and carbon-13 nuclear magnetic resonance spectroscopy and spectroscopic data is recorded in Table 4, Example 21.

EXAMPLE 2

Compounds No 1, 2, 3, 4, 5, 6, 7, 8, 9 and 10 (see Table 1) were prepared from the appropriate benzaldehyde derivative following essentially the same procedure as that described in Example 1 in parts (i) to (iv). Each of the products was characterized by proton nuclear magnetic resonance and/or carbon-13 nuclear magnetic resonance spectroscopy and spectroscopic data is recorded in Table 4, Example 21.

EXAMPLE 3

3-Benzoyloxy-2-[1-(ethoxyimino)propyl]-5-mesitylcyclohex-2-en-1-one (15)

(a) Aqueous 1% sodium hydroxide solution (6 ml) was added to a solution of 2-[1-(ethoxyimino)propyl]-3-hydroxy-5-mesitylcyclohex-2-en-1-one (0.42 g; 1.28 mmole) in acetone (50 ml). The mixture was stirred at room temperature for a period of 5 minutes and then benzoyl chloride (0.2 g) was added dropwise. The mixture was stirred for a further period of 15 minutes and then the solvent was removed by evaporation under reduced pressure using a rotary evaporator. The product was purified by chromatography over silica gel (eluant dichloromethane) to give 3-benzoyloxy-2-[1-(ethoxyimino)propyl]-5-mesitylcyclohex-2-en-1-one (0.38 g; 68.6%) as a pale yellow oil.

(b) A solution of sodium hydroxide (0.12 g) in water (0.7 ml) was added dropwise, with stirring, to a solution of 2-[1-(ethoxyimino)propyl]-3-hydroxy-5-mesitylcyclohex-2-en-1-one (0.89 g) in tetrahydrofuran (9.5 ml). Benzoyl chloride (0.42 g) was added dropwise, with stirring and the mixture was stirred at room temperature for a period of 30 minutes. The solvent was removed by evaporation under reduced pressure and the residue was taken up in dichloromethane and water. The dichloromethane solution was separated, washed twice with water, dried, and the solvent evaporated under reduced pressure. The remaining oil was triturated with petroleum ether (b.p. 40°–60° C.) and the solid which formed was recrystallised from isopropanol to give 3-benzoyloxy-2-[1-(ethoxyimino)propyl]-5-mesitylcyclohex-2-en-1-one (0.79 g) as a solid m.p. 94°–95.5° C.

(c) A mixture of 2-[1-(ethoxyimino)propyl]-3-hydroxy-5-mesitylcyclohex-2-en-1-one (2.4 g), anhydrous methyl ethyl ketone (25 ml) and anhydrous potassium carbonate (1.65 g) was treated dropwise, with stirring, with benzoyl chloride (1.12 g). The mixture was heated under reflux with stirring for a period of 30 minutes and then filtered. The residue was washed with diethyl ether and the solvent from the combined filtrate and washings was evaporated under reduced pressure. The residue was taken up in ethyl acetate and the solution was washed twice with water, dried, and the solvent was evaporated under reduced pressure to give a dark brown oil. The oil was purified by chromatography on preparative thin layer chromatography plates (silica gel; eluent hexane/diethyl ether 75:25) to give 3-benzoyloxy-2-[1-(ethoxyimino)propyl]-5-mesitylcyclohex-2-en-1-one (1.9 g). The product was cahracterized by proton nuclear magnetic resonance spectroscopy and spectroscopic data is recorded in Table 4, Example 21.

EXAMPLE 4

Compounds No 11, 12, 13, 14, 44, 45, 46, 48, 49, 50, 51, 58, 73, 81, 89, 90, 91, 92, 93, 94 and 95 were prepared from compounds No 5, 5, 3, 1, 7, 7, 7, 17, 24, 18, 16, 10, 62, 60, 7, 7, 7, 7, 7, 7, and 7 and the appropriate acid chloride (ethyl bromoacetate for compound no 95) following one of the procedures described in Example 3. Each of the products was characterized by proton nuclear magnetic resonance spectroscopy and spectroscopic data is recorded in Table 4, Example 21.

EXAMPLE 5

2-[1(Allyloxyimino)butyl]-3-hydroxy-5-mesitylcyclohex-2-en-1-one (16)

(i) n-Butyryl chloride (2.3 g; 21.7 mmole) and then pyridine (1.7 g; 21.7 mmole) were added to a stirred mixture of 3-hydroxy-5-mesitylcyclohex-2-en-1-one (5.0 g; 21.7 mmole) and dichloromethane (50 ml) under a nitrogen atmosphere. The mixture was stirred at room temperature for a period of two hours and then poured into slightly acidic water. The organic phase was separated and the aqueous phase was thoroughly extracted with dichloromethane. The combined organic phase and extracts were washed with water, dried over anhydrous magnesium sulfate and the solvent was removed by evaporation under reduced pressure using a rotary evaporator. The residue was dissolved in 1,2-dichloroethane (50 ml), stannic chloride (5.7 g; 22 mmole) was added and the mixture was heated under reflux for a period of 8 hours. The mixture was cooled and poured into water and the aqueous mixture was extracted several times with dichloromethane. The combined organic extracts were dried over anhydrous magnesium sulfate and the solvent was removed by evaporation under reduced pressure using a rotary evaporator. The residue was purified by chromatography over silica gel (eluant dichloromethane) to give 2-butyryl-3-hydroxy-5-mesitylcyclohex-2-en-1-one (2.4 g). Proton nuclear magnetic resonance spectrum (CDCl$_3$: δ in ppm): 1.01 (3H, t); 1.30–1.60 (2H, m); 2.23 (3H, s); 2.37 (6H, s); 2.40–3.45 (7H, m); 6.83 (2H, s); 18.24 (1H, s).

(ii) Allyloxyamine hydrochloride (0.72 g) and then a solution of sodium hydroxide (0.25 g) in water (3 ml) were added to a stirred mixture of 2-butyryl-3-hydroxy-5-mesitylcyclohex-2-en-1-one (1.78 g; 5.9 mmole) and 95% ethanol. The progress of the reaction was monitored using thin layer chromatography on silica gel (eluant dichloromethane). On completion of the reaction the ethanol was removed by evaporation using a rotary evaporator and the residue was extracted with dichloromethane. The organic extract was washed with aqueous 5% hydrochloric acid and then with water and dried over anhydrous magnesium sulfate. The solvent was removed by evaporation under reduced pressure using a rotary evaporator to give the product, 2-[1-(allyloxyimino)butyl]-3-hydroxy-5-mesitylcyclohex-2-en-1-one (1.6 g) as an oil.

The product was characterized by proton nuclear magnetic resonance spectroscopy and the spectroscopic data is recorded in Table 4, Example 21.

EXAMPLE 6

2-[1-(Ethoxyimino)butyl[-3-hydroxy-5-mesitylcyclohex-2-en-1-one (18) was prepared from 2-butyryl-3-hydroxy-5-mesitylcyclohex-2-en-1-one (see Example 5 part (i)) and ethoxyamine hydrochloride following essentially the same procedure as that described in Example 1 part (iv). The product was characterized by proton nuclear magnetic resonance spectroscopy and the spectroscopic data is reported in Table 4, Example 21.

EXAMPLE 7

2-[1-(Allyloxyimino)propyl]-3-hydroxy-5-mesitylcyclohex-2-en-1-one (17) was prepared from 3-hydroxy-5-mesityl-2-propionylcyclohex-2-en-1-one (see Example 1 parts (i) to (iii)) and allyloxyamine hydrochloride following essentially the same procedure as that described in Example 5 part (ii). The product was characterized by proton nuclear magnetic resonance spectroscopy and the spectroscopic data is reported in Table 4, Example 21.

EXAMPLE 8

2-[1-(Propoxyimino)propyl]-3-hydroxy-5-mesitylcyclohex-2-en-1-one (20)

(i) A mixture of 3-hydroxy-5-mesitylcyclohex-2-en-1-one (13.0 g, 0.056 mole), propionic anhydride (26 ml) and propionic acid (26 ml) was stirred and heated at 110° C. until homogeneous. Trifluoromethanesulphonic (0.5 ml) was added and the mixture was heated at 110°-120° C. for 1 hour under an atmosphere of nitrogen. The mixture was poured with stirring into ice-water, neutralized with sodium bicarbonate and then extracted with diethyl ether. The ether extract gave the crude product as a brown oil which was purified by chromatography over silica gel (eluent dichloromethane) to give 3-hydroxy-5-mesityl-2-propionylcyclohex-2-en-1-one (12.5 g, 77%) as a nearly colourless solid, mp 86°-88° C.

(ii) 2-[1-(Propoxyimino)propyl]-3-hydroxy-5-mesitylcyclohex-2-en-1-one (20) was prepared from 3-hydroxy-5-mesityl-2-propionylcyclohex-2-en-1-one and propoxyamine hydrochloride following essentially the same procedure as that described in Example 1 part (iv). The product was characterized by proton magnetic resonance spectroscopy and the spectroscopic data is reported in Table 4, Example 21.

EXAMPLE 9

Compounds No 19, 21, 22, 23, 24, 25, 26, 27, 28, 29, 30, 31, 32, 33, 34, 35, 36, 37, 38, 39, 40, 41, 42, 52, 53, 54, 55, 56, 57, 60, 61, 62, 63, 64, 65, 66, 67, 68, 69, 74, 75, 77, 79 and 82 were prepared from the appropriate 5-arylcyclohexane-1,3-dione (see Example 19), the appropriate carboxylic acid anydride/carboxylic acid mixture and the appropriate hydroxylamine hydrochloride derivative following essentially the same procedure as that described in Example 8. Each of the products was characterized by proton nuclear magnetic resonance spectroscopy and appropriate physical data (melting point for solids and proton chemical shift for liquids is recorded in Table 4, Example 21.

EXAMPLE 10

2-[1-(Ethoxyimino)propyl]-3-hydroxy-5-(pentamethylphenyl)cyclohex-2-en-1-one (60)

(i) Sodium hydride (0.65 g, 0.027 mole) was added to a stirred solution of 3-hydroxy-5-(pentamethylphenyl)-cyclohex-2-en-1-one (6.4 g, 0.024 mole) in dimethylformamide (100 ml) at 60° C. After 15 minutes propionic anhydride (3.3 g, 0.027 mole) was added and the mixture was heated at 110°-120° C. for 3 hours. It was then poured into water (300 ml) and extracted with diethyl ether (2×100 ml). The ether extracts were dried over anhydrous sodium sulfate and the solvent was removed by evaporation under reduced pressure using a rotary evaporator. The product, a brown oil, was purified by chromatography over silica gel (eluent carbon tetrachloride: chloroform (1:1)) to give 3-hydroxy-5-(pentamethylphenyl)-2-propionylcyclohex-2-en-1-one (4.4 g, 56%) as a nearly colourless solid, mp 84° C.

(ii) 2-[1-(Ethoxyimino)propyl]-3-hydroxy-5-(pentamethylphenyl)cyclohex-2-en-1-one (60) was prepared from 3-hydroxy-5-pentamethylphenyl-2-propionylcyclohex-2-en-1-one and ethoxyamine hydrochloride following essentially the same procedure as that described in Example 1 part (iv). The product was characterized by proton magnetic resonance spectroscopy and the spectroscopic data is reported in Table 4, Example 21.

EXAMPLE 11

Compounds No 71, 76, 80, 83 and 86 were prepared from the appropriate 5-arylcyclohexane-1,3-dione (see Example 19), the appropriate carboxylic acid anhydride and the appropriate hydroxylamine hydrochloride derivative following essentially the same procedure as that described in Example 10. Each of the products was characterized by proton nuclear magnetic resonance spectroscopy and spectroscopic data is recorded in Table 4, Example 21.

EXAMPLE 12

2-[1-(Ethoxyimino)ethyl]-3-hydroxy-5-(pentamethylphenyl)cyclohex-2-en-1-one (70)

(i) A mixture of 3-hydroxy-5-(pentamethylphenyl)cyclohex-2-en-1-one (3.00 g; see Example 19) acetic anhydride (10 ml) and acetic acid (10 ml) was stirred and heated under reflux until homogeneous. p-Toluene sulfonic acid (0.5 g) was added and the mixture was refluxed for a further 2 hours. After cooling the mixture was poured into water and the solution was extracted with ether. The ether extract was washed several times with water, dried over anhydrous magnesium sulfate and then evaporated to dryness. The product, a brown oil, was purified by column chromatography over silica gel (eluent dichloromethane) to give 3-hydroxy-5-pentamethylphenyl-2-acetyl-cyclohex-2-en-1-one (1.50 g) as a crystalline solid, mp 183° C.

(ii) 2-[1-(Ethoxyimino)ethyl]-3-hydroxy-5-(pentamethylphenyl)cyclohex-2-en-1-one (70) was prepared from 3-hydroxy-5-pentamethylphenyl-2-acetyl-cyclohex-2-en-1-one and ethoxyamine hydrochloride following essentially the same procedure as that described in Example 1 part (iv). The product was characterized by proton magnetic resonance spectroscopy and the spectroscopic data is reported in Table 4, Example 21.

EXAMPLE 13

2-[1-(Ethoxyimino)benzyl]-3-hydroxy-5-(2,5-dimethylphenyl)cyclohex-2-en-1-one (87)

(i) Sodium hydride (0.53 g, 0.022 mole) was added to a stirred solution of 3-hydroxy-5-(2,5-dimethylphenyl)-cyclohex-2-en-1-one (4.32 g, 0.020 mole; see Example 19) in dimethylformamide (60 ml) at 60° C. After 30 minutes benzoic anhydride (5.00 g, 0.022 mole) was added and the mixture was heated at 110°-120° C. for 4 hours. It was then poured into water (300 ml), acidified to pH 3 with hydrochloric acid and extracted with diethyl ether (2×100 ml). The ether extracts were washed with water, dried over anhydrous sodium sulfate and evaporated under reduced pressure. The crude product, a brown oil, was dissolved in diethyl ether (200 ml), filtered, shaken with a saturated aqueous cupric acetate solution (300 ml) and then the mixture was evaporated to dryness under reduced pressure. The crude solid was collected, washed successively with hot water, cold water, diethyl ether and hexane, then air dried to give the copper salt of 2-benzoyl-5-(2,5-dimethylphenyl)-3-hydroxy-cyclohex-2-en-1-one (6.00 g) as a pale green solid mp 182°–185° C.

The copper salt, suspended in water, was acidified with 3N hydrochloric acid and then extracted into diethyl ether. The ether extract was washed with water, dried over anhydrous sodium sulfate and evaporated under reduced pressure to give 2-benzoyl-5-(2,5-dimethylphenyl)-3-hydroxy-cyclohex-2-en-1-one (4.20 g, 65%) as a pale yellow oil. Proton nuclear magnetic resonance spectrum (CDCl$_3$: $\delta$ in ppm): 2.33 (6H, s); 2.45–2.90 (4H, m); 3.30–3.70 (1H, m); 6.90–7.15 (3H, brs); 7.30–7.80 (3H, m); 8.00–8.30 (2H, m).

(ii) 2-[1-(Ethoxyimino)benzyl]-3-hydroxy-5-(2,5-dimethylphenyl)cyclohex-2-en-1-one (87) was prepared from 3-hydroxy-5-(2,5-dimethylphenyl)-2-benzoyl-cyclohex-2-en-1-one and ethoxyamine hydrochloride following essentially the same procedure as that described in Example 1 part (iv). The product was characterized by proton magnetic resonance spectroscopy and the spectroscopic data is reported in Table 4, Example 21.

EXAMPLE 14

Sodium salt of 2-[1-(ethoxyimino)propyl]-3-hydroxy-5-mesitylcyclohex-2-en-1-one (43)

A solution of sodium hydroxide (0.45 g) in water (2 ml) was added to a solution of 2-[1-(ethoxyimino)propyl]-3-hydroxy-5-mesitylcyclohex-2-en-1-one (3.86 g) in acetone (50 ml). The solvent was removed under reduced pressure using a rotary evaporator to yield the title compound as a yellow solid (3.98 g, 99%), mp 196° C. (decomp.).

EXAMPLE 15

Compounds No 47 and 59 (see Table 1) were prepared from the appropriate 2-[1-(alkoxyiminopropyl]-3-hydroxy 5-(substituted phenyl)cyclohex-2-en-1-one derivative and sodium hydroxide following essentially the same procedure as that described in Example 11. The products were characterized by mp data which is recoreded in Table 4, Example 21.

EXAMPLE 16

Copper salt of 2-[1-(ethoxyimino)butyl]-3-hydroxy-5-(pentamethylphenyl)cyclohex-2-en-1-one (84)

2-[1-(Ethoxyimino)butyl]-3-hydroxy-5-(pentamethylphenyl)cyclohex-2-en-1-one (400 mg, 1.1 mmole) in diethyl ether (50 ml) was shaken with a saturated aqueous cupric acetate solution (50 ml). The mixture was then evaporated to dryness under reduced pressure. The solid residue was washed successively with hot water, cooled water and diethyl ether, then dried to give the copper salt of 2-[1-(ethoxyimino)butyl]-3-hydroxy-5-(pentamethylphenyl)cyclohex-2-en-1-one (390 mg, 88%) as a pale green solid, mp 210° C.

EXAMPLE 17

Nickel salt of 2-[1-(ethoxyimino)butyl]-3-hydroxy-5-(pentamethylphenyl)cyclohex-2-en-1-one (85) was prepared following an analogous procedure to that described in Example 16. The product was obtained as a solid and its melting point is recorded in Table 4, Example 21.

EXAMPLE 18

Tetrabutylammonium salt of 2-[1-(ethoxyimino)propyl]-3-hydroxy-5-(2,4,6-trimethylphenyl)cyclohex-2-en-1-one (88)

To a solution of 2-[1-(ethoxyimino)propyl]-3-hydroxy-5-(2,4,6-trimethylphenyl)cyclohex-2-en-1-one (329 mg; 10 mmole) in methanol (5 ml) was added a 25% methanolic solution of tetra-n-butylammonium hydroxide (2.0 ml). The mixture was kept at room temperature for 3 hours and then evaporated to dryness under reduced pressure using a rotary evaporator. The residue was taken up in dichloromethane (15 ml) and water (15 ml). The layers were separated and the organic layer washed with water (2×10 ml), dried over anhydrous sodium sulfate and evporated under reduced pressure to afford the tetrabutylammonium salt of 2-[1-(ethoxyimino)propyl]-3-hydroxy-5-(2,4,6-trimethylphenyl)cyclohex-en-1-one (340 mg), as a pale brown oil. The product was characterized by proton magnetic resonance spectroscopy and the spectroscopic data is reported in Table 4, Example 21.

EXAMPLE 19

The 5-arylcyclohexane-1,3-diones of formula IX used in the preparation of the compounds of formula I were prepared from the appropriate benzaldehyde derivative following essentially the same procedure as that described in Example 1 parts (i) and (ii).

The majority of the 5-arylcyclohexane-1,3-diones of formula IX were obtained as solids and were characterized by their nuclear magnetic resonance spectra. For convenience, proton nuclear magnetic resonance spectroscopic (pmr) data is recorded in Table 2 below.

TABLE 2

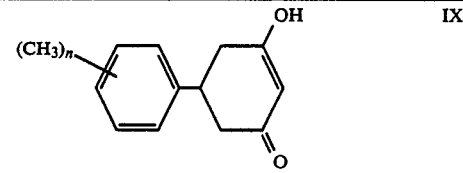

IX

| Compound (CH$_3$)$_n$ | Appearance | Proton Chemical Shift $\delta$ in ppm (D$_6$-DMSO) |
|---|---|---|
| 2,3-(CH$_3$)$_2$ | yellow solid; mp 209° C. | 2.0–2.8 (10H,m); 3.4–3.7 (1H,m); 5.28 (1H,s); 7.00 (3H,m); 11.2 (1H,brs) |
| 2,4-(CH$_3$)$_2$ | yellow solid; mp 167° C. | 2.0–2.8 (10H,m); 3.40 (1H, m); 5.25 (1H,s); 6.9–7.3 (3H,m); 11.15 (1H,brs). |
| 2,5-(CH$_3$)$_2$ | pale yellow solid; mp 180° C. | 2.0–3.8 (11H,m); 5.30 (1H,s); 6.8–7.3 (3H,m); 11.5 (1H,brs) |
| 2,6-(CH$_3$)$_2$ | orange solid | 2.0–3.8 (11H,m); 5.28 (1H,s); 6.96 (3H,m); 11.2 (1H,brs) |
| 3,4-(CH$_3$)$_2$ | pale yellow solid; mp 162° C. | 2.0–2.6 (11H,m); 5.25 (1H,s); 7.00 (3H,m); 11.0 (1H,brs) |
| 3,5-(CH$_3$)$_2$ | yellow solid; mp 170° C. | 2.0–3.3 (11H,m); 5.25 (1H,s); 6.8–7.0 (3H,m); 11.5 (1H,brs) |

TABLE 2-continued

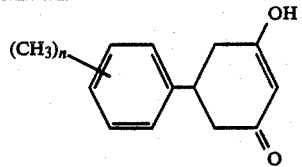

| Compound (CH$_3$)$_n$ | Appearance | Proton Chemical Shift δ in ppm (D$_6$-DMSO) |
|---|---|---|
| 2,3,4-(CH$_3$)$_3$ | brown solid | 2.0–2.7 (13H,m); 3.0–3.8 (1H,m); 5.28 (1H,s); 6.96 (2H,m); 11.2 (1H,brs) |
| 2,3,5-(CH$_3$)$_3$ | yellow solid; mp 206° C. | 2.20 (6H,s); 2.30 (3H,s); 2.3–3.0 (4H,m); 3.50 (1H,m); 5.25 (1H,s); 6.90 (1H,s); 7.10 (1H,s); 11.0 (1H,brs) |
| 2,3,6-(CH$_3$)$_3$ | solid | 1.9–3.1 (13H,m); 3.80 (1H,m); 5.28 (1H,s); 6.91 (2H,m); 11.3 (1H,brs) |
| 2,4,5-(CH$_3$)$_3$ | brown solid; mp 112° C. | Not recorded |
| 2,4,6-(CH$_3$)$_3$ | solid; mp 165° C. | 2.0–4.1 (14H,m); 5.20 (1H,s); 6.80 (2H,s); 11.2 (1H,brs) |
| 3,4,5-(CH$_3$)$_3$ | colorless solid; mp 206° C. | 2.06 (3H,s); 2.20 (6H,s); 2.30–2.85 (4H,m); 308 (1H,m); 5.28 (2H,s); 6.91 (2H,s); 11.4 (1H,brs) |
| 2,3,4,5-(CH$_3$)$_4$ | colorless solid; mp 223° C. | Not recorded |
| 2,3,4,6-(CH$_3$)$_4$ | yellow solid; mp 184° C. | 2.0–2.4 (12H,m); 2.4–3.2 (4H,m); 3.60 (1H,m); 5.25 (1H,s); 6.80 (1H,s); 11.2 (1H,brs) |
| 2,3,4,5,6-(CH$_3$)$_5$ | pale yellow solid; mp 258° C. | 2.20 (12H,s); 2.4–3.2 (4H,m); 3.60 (1H,m); 5.25 (1H,s); 6.80 (1H,s); 11.2 (1H,brs) |
| 2,3,4,5,6-(CH$_3$)$_5$ | colorless solid; mp 235° C. | 2.09 (3H,s); 2.11 (6H,s); 2.20–2.50 (4H,m); 3.93 (1H,m); 5.15 (1H,s); 11.0 (1H,brs) |

EXAMPLE 20

The 2-acyl-5-arylcyclohexane-1,3-diones of formula XIII used in the preparation of the compounds of formula I were prepared from the corresponding 5-arylcyclohexane-1,3-dione of formula IX by acylation using the appropriate acyl derivative following essentially the same procedure as that described in one of Examples 1 part (iii), 5 part (i), 8 part (i), 10 part (i), 12 part (i) and 13 part (i).

The majority of the 2-acyl-5-arylcyclohexane-1,3-diones of formula XIII were obtained as oils and were characterized by their nuclear magnetic resonance spectra. For convenience, proton nuclear magnetic resonance spectroscopic (pmr) data is recorded in Table 3 below.

TABLE 3

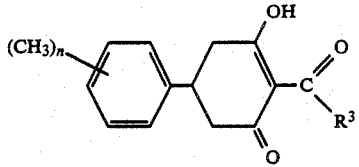

| Compound (CH$_3$)$_n$ | R$^3$ | Appearance | Proton Chemical Shift δ in ppm (CDCl$_3$) |
|---|---|---|---|
| 2,3-(CH$_3$)$_2$ | C$_2$H$_5$ | pale yellow solid; mp 100° C. | 1.20 (3H,t); 2.25 (6H, 2×s); 2.3–4.0 (7H,m); 7.00 (3H,s); 18.20 (1H,s) |
| 2,4-(CH$_3$)$_2$ | C$_2$H$_5$ | orange oil | 1.10 (3H,t); 2.30 (6H,s); 2.4–3.0 (4H,m); 3.10 (2H,q); 3.40 (1H,m); 7.00 (3H,s); 18.10 (1H,s) |
| 2,5-(CH$_3$)$_2$ | C$_2$H$_5$ | oil | 1.20 (3H,t); 2.25 (6H,s); 2.40–3.80 (7H,m); 7.00 (3H,m); 18.20 (1H,s) |
| 2,5-(CH$_3$)$_2$ | C$_6$H$_5$ | pale yellow oil | 2.33 (6H,s); 2.45–2.90 (4H,m); 3.30–3.70 (1H,m); 6.90–7.15 (3H,brs); 7.30–7.80 (3H,m); 8.00–8.30 (2H,m) |
| 2,6-(CH$_3$)$_2$ | C$_2$H$_5$ | yellow oil | 1.20 (3H,t); 2.40 (6H,s); 2.4–4.0 (7H,m); 7.00 (3H,s); 18.10 (1H,s) |
| 3,4-(CH$_3$)$_2$ | C$_2$H$_5$ | pale yellow solid; mp 100° C. | 1.16 (3H,t); 2.24 (6H,s); 2.56–3.28 (7H,m); 6.96 (3H,m); 18.24 (1H,s) |
| 3,4-(CH$_3$)$_2$ | n-C$_3$H$_7$ | pale yellow solid; mp 76° C. | 1.00 (3H,t); 1.65 (2H,m); 2.25 (6H,s); 2.5–3.3 (7H,m); 6.98 (3H,m); 18.25 (1H,s) |
| 3,5-(CH$_3$)$_2$ | C$_2$H$_5$ | yellow solid; mp 113° C. | 1.10 (3H,t); 2.30 (6H,s); 2.5–3.4 (7H,m); 6.8–7.0 (3H,m); 18.20 (1H,s) |
| 2,3,4-(CH$_3$)$_3$ | C$_2$H$_5$ | brown oil | 1.20 (3H,t); 2.20 (9H,m); 2.50–2.90 (4H,m); 3.10 (2H,q); 3.60 (1H,m); 6.95 (2H,m); 18.10 (1H,s) |
| 2,3,5-(CH$_3$)$_3$ | C$_2$H$_5$ | yellow solid; mp 107° C. | 1.20 (3H,t); 2.20 (3H,s); 2.25 (6H,s); 2.45–3.20 (6H,m); 3.60 (1H,m); 6.80 (1H,s) 6.85 (1H,s); 18.20 (1H,s) |
| 2,3,6-(CH$_3$)$_3$ | C$_2$H$_5$ | orange oil | 1.20 (3H,t); 2.25 (3H,s); 2.31 (3H,s); 2.37 (3H,s); 2.5–3.4 (6H,m); 3.82 (1H,m); 6.94 (2H,m); 18.18 (1H,s) |
| 2,4,5-(CH$_3$)$_3$ | C$_2$H$_5$ | yellow solid; mp 111° C. | 1.20 (3H,t); 2.30 (9H,s); 2.4–4.0 (7H,m); 7.00 (2H,s); 18.20 (1H,s) |
| 2,4,6-(CH$_3$)$_3$ | CH$_3$ | colorless solid; | 2.24 (3H,s); 2.36 (6H,s); 2.64 (3H,s); 2.65–4.00 (5H,m); 6.84 (2H,s); 18.17 (1H,s) |
| 2,4,6-(CH$_3$)$_3$ | C$_2$H$_5$ | solid; mp 86–88° C. | 1.60 (3H,t,J=8Hz); 2.24 (3H,s); 2.37 (6H,s); 2.64–5.26 (7H,m); 6.84 (2H,m); 18.26 (1H,s) |
| 2,4,6-(CH$_3$)$_3$ | n-C$_3$H$_7$ | oil | 1.01 (3H,t); 1.30–1.60 (2H,m); 2.23 (3H,s); 2.37 (6H,s); 2.40–3.45 (7H,m); 6.83 (2H,s); 18.24 (1H,s) |
| 3,4,5-(CH$_3$)$_3$ | C$_2$H$_5$ | solid; mp 93° C. | 1.14 (3H,t); 2.14 (3H,s); 2.28 (6H,s); 2.3–3.4 (7H,m); 6.79 (2H,s); 18.12 (1H,s) |
| 2,3,4,5-(CH$_3$)$_4$ | C$_2$H$_5$ | pale yellow solid; mp 97° C. | 1.15 (3H,t); 2.20 (12H,m); 2.40–2.90 (4H,m); 3.10 (2H,q); 3.55 (1H,m); 6.80 (1H,s); 18.10 (1H,s) |
| 2,3,4,6-(CH$_3$)$_4$ | C$_2$H$_5$ | brown oil | 1.20 (3H,t); 2.1–2.4 (12H,4×S); 2.4–4.0 (7H,m); 6.90 (1H,s); 18.00 (1H,s) |
| 2,3,4,6-(CH$_3$)$_4$ | n-C$_3$H$_7$ | brown oil | 1.00 (3H,t); 1.65 (2H,m); |

TABLE 3-continued

Structure XIII: A cyclohexenone with OH group, substituted with (CH₃)ₙ-phenyl group and C(=O)R³ group.

| Compound (CH₃)ₙ | R³ | Appearance | Proton Chemical Shift δ in ppm (CDCl₃) |
|---|---|---|---|
| (CH₃)₄ | | | 2.1–2.4 (12H,4×s); 2.4–3.4 (6H,m); 3.80 (1H,m); 6.80 (1H,s); 18.30 (1H,s) |
| 2,3,5,6-(CH₃)₄ | $C_2H_5$ | brown oil | 1.20 (3H,t); 2.30 (12H, s); 2.4–4.0 (7H,m); 6.80 (1H,s); 18.00 (1H,s) |
| 2,3,4,5,6-(CH₃)₅ | $CH_3$ | solid; mp 183° C. | Not recorded |
| 2,3,4,5,6-(CH₃)₅ | $C_2H_5$ | solid; mp 84° C. | Not recorded |
| 2,3,4,5,6-(CH₃)₅ | n-$C_3H_7$ | brown oil | 1.00 (3H,t); 1.70 (2H,m); 2.18 (9H,s); 2.25 (6H,s); 2.25 (6H,s); 2.25–3.40 (6H,m); 3.90 (1H,m); 18.10 (1H,s) |

EXAMPLE 21

The majority of the compounds of the invention were obtained as oils and were characterized by, and can be identified by their nuclear magnetic resonance spectra. For convenience proton nuclear magnetic resonance spectroscopic (pmr) data is recorded in Table 4a below and carbon-13 nuclear magnetic resonance spectroscopic data is recorded in Table 4b below.

TABLE 4

Part (a)

| Compound No | Appearance | Proton Chemical Shift δ in ppm (CDCl₃) |
|---|---|---|
| 1 | Solid; mp 70° C. | 1.04–1.39 (6H,m); 2.28 (3H,s); 2.32 (3H,s); 2.63–4.01 (9H,m); 7.07 (3H,m); 15.03 (1H,br.s). |
| 2 | Pale yellow oil | 1.10–1.39 (6H,m); 2.28 (3H,s); 2.31 (3H,s); 2.40–2.70 (4H,m); 2.97 (2H,q,J=8 Hz); 3.52 (1H,m); 4.10 (2H,q,J=8 Hz); 7.00–7.15 (3H,m); 15.0 (1H,br.s). |
| 3 | Pale yellow oil | 1.11–1.40 (6H,m); 2.31 (6H,s); 2.64–3.02 (6H,m); 3.53 (1H,m); 4.12 (2H,q,J=8 Hz); 7.00–7.23 (3H,m); 15.03 (1H,br.s). |
| 4 | Pale yellow oil | 1.12–1.40 (6H,m); 2.41 (6H,s); 2.62–3.14 (6H,m); 3.85 (1H,m); 4.12 (2H,q,J=8 Hz); 7.01 (3H,s); 15.03 (1H,br.s). |
| 5 | Pale yellow oil | 1.10–1.37 (6H,m); 2.22 (6H,s); 2.60–2.92 (7H,m); 4.07 (2H,q, J=8 Hz); 6.97–7.04 (3H,m); 14.70 (1H,br.s). |
| 6 | Pale yellow oil | 1.08–1.39 (6H,m); 2.30 (6H,s); 2.65–3.00 (7H,m); 4.10 (2H,q, J=8 Hz); 6.85 (3H,s); 15.0 (1H,s). |
| 7 | Pale yellow oil | 1.13–1.48 (6H,m); 2.23 (3H,s); 2.37 (6H,s); 2.60–4.23 (9H,m); 6.83 (2H,s); 14.99 (1H,s). |
| 8 | Pale yellow oil | 1.07–1.40 (6H,m); 2.21 (6H,s); 2.27 (3H,s); 2.36–3.07 (6H,m); 3.42 (1H,m); 4.10 (2H,q,J=8 Hz); 6.95–7.23 (2H,m); 15.0 (1H,br.s). |
| 9 | Pale yellow oil | 1.07–1.41 (6H,m); 2.23 (6H,s); 2.27 (6H,s); 2.41–3.16 (6H,m); 4.00–4.12 (3H,m); 6.91 (1H,s); 15.0 (1H,br.s). |
| 10 | Pale yellow oil | 1.07–1.41 (6H,m); 2.16 (3H,s); 2.24 (3H,s); 2.32 (3H,s); 2.35 (3H,s); 2.40–3.35 (6H,m); 3.41–4.07 (3H,m); 6.86 (1H,s); 15.0 (1H,br.s). |
| 11 | Pale yellow oil | 0.92–1.74 (6H,m); 2.22 (6H,s); 2.24–3.15 (7H,m); 3.99 (1H,q, J=8 Hz); 7.04–8.10 (8H,m). |
| 12 | Pale yellow oil | 0.90–1.34 (6H,m); 2.16 (3H,s); 2.22 (6H,s); 2.24–3.15 (7H,m); 4.13 (2H,q,J=8 Hz); 7.00–7.25 (3H,m). |
| 13 | Pale yellow oil | 1.10–1.39 (6H,m); 2.31 (6H,s); 2.64–3.02 (6H,m); 3.53 (1H,m); 4.12 (2H,q,J=8 Hz); 7.00–7.23 (3H,m); 7.38–8.10 (5H,m). |
| 14 | Pale yellow oil | 1.04–1.39 (6H,m); 2.28 (3H,s); 2.32 (3H,s); 2.63–4.01 (9H,m); 7.07 (3H,m); 7.38–8.08 (5H,m). |
| 15 | Pale yellow oil | 1.13–1.48 (6H,m); 2.24 (3H,s); 2.42 (6H,s); 2.42–3.90 (9H,m); 6.85 (2H,s); 7.24–8.08 (5H,m). |
| 16 | Pale yellow oil | 1.05 (3H,t); 1.30–1.60 (2H,m); 2.23 (3H,s); 2.37 (6H,s); 2.40–3.90 (7H,m); 4.61 (2H,m); 5.34 (2H,m); 5.80 (1H,m); 6.80 (2H,s); 14.70 (1H,s). |
| 17 | Pale yellow oil | 1.10 (3H,t); 2.21 (3H,s); 2.37 (6H,s); 2.5–3.95 (8H,m); 4.52 (2H,m); 5.34 (2H,m); 5.80 (1H,m); 6.80 (2H,s); 14.7 (1H,s). |
| 18 | Pale yellow oil | 1.05 (3H,t); 1.32 (3H,t); 1.66 (2H,m); 2.23 (3H,s); 2.37 (6H,s); 2.4–3.95 (7H,m); 4.15 (2H,q); 6.83 (2H,s); 15.13 (1H,s). |
| 19 | pale yellow oil | 1.32 (3H,t); 2.23 (3H,s); 2.37 (6H,s); 2.41 (3H,s); 2.4–4.0 (5H,m); 4.12 (2H,q); 6.83 (2H,s); 14.7 (1H,s). |
| 20 | solid; mp 114° C. | 0.99 (3H,t); 1.21 (3H,t); 1.69 (2H,m); 2.23 (3H,s); 2.37 (6H,s); 2.3–3.9 (7H,m); 4.01 (2H,t); 6.83 (2H,s); 14.99 (1H,s). |
| 21 | solid; mp 70–72° C. | 0.95 (3H,t); 1.20 (3H,t); 1.2–1.8 (4H,m); 2.24 (3H,s); 2.37 (6H,s); 2.3–3.9 (5H,m); 2.95 (2H,q); 4.06 (2H,t); 6.84 (2H,s); 15.05 (1H,s). |
| 22 | solid; mp 89–91° C. | 1.19 (3H,t); 1.77 (3H,d,J=6 Hz); 2.24 (3H,s); 2.37 (6H,s); 2.3–3.9 (5H,m); 2.95 (2H,q); 4.47 (2H,d, J=Hz); 5.6–5.9 (2H,m); 6.83 (2H,s), 14.9 (1H,s). |
| 23 | solid; mp 69–71° C. | 1.19 (3H,t); 2.24 (3H,s), 2.37 (6H,s); 2.3–3.9 (5H,m); 2.94 (2H,q); 4.12 (2H,t); 5.0–5.3 (2H,m); 5.6–6.0 (1H,m); 6.84 (2H,s); 14.8 (1H,brs). |
| 24 | pale yellow oil | 1.19 (3H,t); 2.24 (3H,s); 2.37 (6H,s); 2.4–3.9 (8H,m); 4.64 (2H, d,J=2.4 Hz); 6.84 (2H,s); 13.90 (1H,s). |
| 25 | pale yellow oil | 1.20 (3H,t); 2.24 (3H,s); 2.37 (6H, s); 2.4–3.9 (5H,m); 2.95 (2H,q); 4.10–4.20 (1H,m); 4.36–4.48 (2H, m); 4.89–4.98 (1H,m); 6.84 (2H, s); 14.06 (1H,brs). |
| 26 | pale yellow oil | 1.22 (3H,t); 2.24 (3H,s); 2.38 (6H,s); 2.4–3.9 (5H,m); 2.99 (2H,q); 4.60 (2H,s); 5.47 (2H,s); 6.84 (2H,s); 14.5 (1H,brs). |
| 27 | pale yellow oil | 1.19 (3H,t); 2.23 (3H,s); 2.35 (6H,s); 2.4–3.9 (5H,m); 2.90 (2H, q); 5.06 (2H,s); 6.82 (2H,s); 7.36 (5H,m); 14.3 (1H,s). |
| 28 | pale yellow oil | 1.18 (3H,t); 2.24 (3H,s); 2.36 (6H,s); 2.4–3.9 (7H,m); 5.03 (2H, s); 6.83 (2H,s); 7.33 (4H,s); 14.16 (1H,s). |
| 29 | pale yellow oil | 1.18 (3H,t); 2.24 (3H,s); 2.36 (6H,s); 2.4–3.9 (7H,m); 5.02 (2H, s); 6.83 (2H,s); 7.37 (4H,dofd); |

TABLE 4-continued

Part (a)

| Compound No | Appearance | Proton Chemical Shift δ in ppm (CDCl₃) |
|---|---|---|
| | | 14.5 (1H,s). |
| 30 | solid; mp 68-70° C. | 1.18 (3H,t); 2.24 (3H,s); 2.36 (6H,s); 2.3-3.9 (7H,m); 5.03 (2H, s); 6.83 (2H,s); 7.0-7.4 (4H,m); 14.29 (1H,s). |
| 31 | pale yellow oil | 1.18 (3H,t); 2.22 (3H,s); 2.34 (9H,s); 2.3-3.9 (7H,m); 5.01 (2H, s); 6.82 (2H,s); 7.21 (4H,dofd); 14.45 (1H,s). |
| 32 | solid; mp <50° C. | 1.21 (3H,t); 2.24 (3H,s); 2.35 (6H,s); 2.4-3.9-(7H,m); 5.18 (2H,s); 6.83 (2H,s); 7.88 (4H, dofd); 13.74 (1H,s). |
| 33 | pale yellow oil | 1.20 (3H,t); 2.22 (3H,s); 2.34 (6H,s); 2.4-3.9 (7H,m); 5.02 (2H, s); 6.81 (2H,s); 7.2-7.34 (4H,m); 14.03 (1H,s). |
| 34 | solid; mp <50° C. | 1.20 (3H,t); 2.23 (3H,s); 2.35 (6H,s); 2.4-3.9 (7H,m); 5.15 (2H, s); 6.83 (2H,s); 7.19-7.40 (3H,m); 14.0 (1H,s). |
| 35 | solid; mp 76° C. | 0.9-1.2 (6H,m); 1.3-1.8 (6H,m); 2.25 (3H,s); 2.38 (6H,s); 2.4-3.9 (7H,m); 4.07 (2H,q); 6.84 (2H,s); 14 (1H,brs). |
| 36 | solid; mp 68-70° C. | 1.00 (3H,t); 1.5-1.8 (5H,m); 2.24 (3H,s); 2.37 (6H,s); 2.4-3.9 (7H, m); 4.46 (2H,d,J=6 Hz); 5.4-6.0 (2H,m); 6.84 (2H,s); 14 (1H,brs). |
| 37 | solid; mp 70-71° C. | 1.00 (3H,t); 1.3-1.6 (2H,m), 2.22 (3H,s); 2.36 (6H,s); 2.4-3.9 (7H,m); 4.10 (2H,q); 5.0-5.3 (2H, m); 5.6-6.0 (1H,m); 6.82 (2H,s); 14.6 (1H,s). |
| 38 | pale yellow oil | 0.97 (3H,t); 1.6 (2H,m); 2.24 (3H, s); 2.37 (6H,s); 2.4-3.7 (8H,m); 4.65 (2H,d,J=2.4 Hz); 6.84 (2H,s); 14.1 (1H,s). |
| 39 | pale yellow oil | 1.00 (3H,t); 1.3-1.6 (2H,m); 2.24 (3H,s); 2.38 (6H,s); 2.4-3.9 (7H, m); 4.1-4.2 (1H,m); 4.36-4.51 (2H, m); 4.89-4.98 (1H,m); 6.84 (2H,s); 14 (1H,brs). |
| 40 | solid; mp 92-94° C. | 1.00 (3H,t); 1.3-1.6 (2H,m); 2.24 (3H,s); 2.37 (6H,s); 2.4-3.9 (7H,m); 4.59 (2H,s); 5.48 (2H,s); 6.84 (2H,s); 14 (1H,brs). |
| 41 | pale yellow oil | 0.99 (3H,t); 1.4-1.7 (2H,m); 2.21 (3H,s); 2.34 (6H,s); 2.4-3.9 (7H, m); 5.00 (2H,s); 6.81 (2H,s); 7.30 (4H,s); 14.23 (1H,s). |
| 42 | pale yellow oil | 0.99 (3H,t); 1.4-1.7 (2H,m); 2.23 (3H,s); 2.35 (6H,s); 2.4-3.9 (7H, m); 5.00 (2H,s); 6.83 (2H,s); 7.36 (4H,dofd); 14 (1H,brs). |
| 43 | pale yellow solid, mp 196° C. (decomp.) | Not recorded |
| 44 | pale brown solid; mp 45-50° C. | 0.90-1.20 (6H,m); 2.10 (3H,s); 2.30 (6H,s); 2.2-3.7 (6H,m); 3.99 (3H,m); 6.85 (2H,s); 8.10 (4H, dofd). |
| 45 | pale brown solid, mp <50° C. | 1.0-1.2 (6H,m); 2.10 (3H,s); 2.30 (6H,s); 2.3-3.6 (6H,m); 3.99 (3H, m); 6.80 (2H,s); 8.20 (4H,m). |
| 46 | pale brown solid; mp 83° C. | 1.0-1.3 (6H,m); 2.25 (3H,s); 2.45 (6H,s); 2.5-4.2 (9H,m); 6.80 (2H,s); 9.20 (3H,m). |
| 47 | yellow solid; mp 200° C. (decomp.) | Not recorded |
| 48 | pale yellow oil | 1.04 (3H,t); 2.24 (3H,s); 2.42 (6H,s); 2.4-3.7 (5H,m); 4.46 (2H, d,J=6 Hz); 5.12 (2H,m); 5.64 (1H, m), 6.85 (2H,s); 7.2-8.1 (5H,m). |
| 49 | Pale yellow oil | 1.04 (3H,t); 2.22 (3H,s); 2.40 (6H,s); 2.4-3.9 (7H,m); 4.55 (2H, d,J=2.4 Hz); 6.82 (2H,s); 7.4-8.1 (5H,m). |
| 50 | Pale orange oil | 0.83-1.10 (6H,m); 1.53 (2H,m); 2.23 (3H,s); 2.42 (6H,s); 2.4-3.7 (7H,m); 4.00 (2H,q,J=8 Hz); 6.84 (2H,s); 7.28-8.08 (5H,m). |
| 51 | orange oil | 0.92 (3H,t); 1.53 (2H,m); 2.23 (3H,s); 2.42 (6H,s); 2.5-4.4 (7H, m); 4.46(2H,d); 4.96 (2H,dofd); 5.77 (1H,m); 6.84 (2H,s); 7.2-8.1 (5H,m). |
| 52 | pale brown oil | 1.10 (3H,t); 1.25 (3H,t); 2.20 (3H,s); 2.26 (3H,s); 2.4-3.7 (5H,m); 2.96 (2H,q); 4.11 (2H,q); 6.99 (2H,s); 14.98 (1H,brs). |
| 53 | yellow oil | 1.10-1.40 (6H,2×t); 2.20 (3H,s); 2.26 (6H,s); 2.86-3.01 (6H,m); 3.56 (1H,m); 4.11 (2H,q); 6.89 (2H,s); 15.02 (1H,s). |
| 54 | pale yellow oil | 1.17 (3H,t); 1.34 (3H,t); 2.15 (3H,s); 2.28 (6H,s); 2.5-3.4 (7H,m); 4.04 (2H,q); 6.87 (2H,s); 14.95 (1H,s). |
| 55 | yellow oil | 0.92-1.40 (6H,m), 1.62 (2H,m); 2.16 (3H,s); 2.24 (3H,s); 2.32 (3H,s); 2.34 (3H,s); 2.6-3.0 (6H, m); 3.74-4.23 (3H,m); 6.85 (1H,s); 15.1 (1H,s). |
| 56 | pale brown oil | 1.19 (3H,t); 2.14 (3H,s); 2.24 (3H,s); 2.32 (3H,s); 2.34 (3H,s); 2.4-3.14 (6H,m); 3.80 (1H,m); 4.53 (2H,d,J=6 Hz); 4.35 (2H,m); 5.90 (1H,m); 6.83 (1H,s); 14.5 (1H,brs). |
| 57 | yellow oil | 0.97 (3H,t); 1.62 (2H,m); 2.13 (3H,s); 2.22 (3H,s); 2.29 (3H,s); 2.32 (3H,s); 2.60-3.02 (6H,m); 3.80 (1H,m); 4.51 (2H,d,J=6 Hz); 5.24 (2H,m); 5.80 (1H,m); 6.83 (1H,s); 14.65 (1H,s). |
| 58 | pale brown oil | 0.99 (3H,t); 1.17 (3H,t); 2.17 (3H,s); 2.25 (3H,s); 2.39 (3H,s); 2.49 (3H,s); 2.4-3.5 (6H,m); 3.5-4.13 (3H,m); 6.87 (1H,s); 7.25-7.56 (3H,m); 8.03-8.09 (2H,m) |
| 59 | yellow solid mp 250° C. (decomp.) | Not recorded |
| 60 | pale yellow solid, mp 121° C. | 1.00-1.30 (6H,m); 2.10 (9H,s); 2.15 (6H,s); 2.2-3.3 (6H,m); 3.6-4.15 (3H,m); 14.80 (1H,s). |
| 61 | pale yellow solid; mp <50° C. | 1.21 (3H,t); 2.14 (9H,s); 2.32 (6H,s); 2.43-3.86 (6H,m); 4.00 (1H,m); 4.50 (2H,d,J=7 Hz); 5.37 (2H,m); 5.89 (1H,m); 14.53 (1H,s). |
| 62 | pale brown solid; mp 116° C. | 1.00-1.32 (6H,2×t); 1.62 (2H,m); 2.22 (9H,s); 2.32 (6H,s); 2.4-3.1 (6H,m); 3.99-4.23 (3H,m); 15.06 (1H,s). |
| 63 | pale brown oil | 1.00 (3H,t); 1.63 (2H,m); 2.21 (9H,s); 2.31 (6H,s); 2.49-3.00 (6H,m); 4.00 (1H,m); 4.52 (2H,d, J=7 Hz); 5.36 (2H,m); 5.88 (1H,m); 14.60 (1H,s). |
| 64 | yellow oil | 1.04-1.40 (6H,2×t); 2.19-2.27 (12H,m); 2.67 (4H,m); 2.97 (4H,q); 3.59 (1H,m); 4.11 (2H,q); 6.87 (1H,s); 15.0 (1H,brs). |
| 65 | pale yellow oil | 0.98 (3H,t); 1.18 (3H,t); 1.68 (2H,m); 2.24 (6H,s); 2.5-3.4 (7H,m); 4.00 (2H,t); 6.9-7.1 (3H,m); 14 (1H,brs). |
| 66 | pale yellow oil | 1.17 (3H,t); 2.25 (6H,s); 2.5-3.4 7H,m); 4.54 (2H,d,J=6.4 Hz); 5.35 (2H,m); 5.90 (1H,m); 6.9-7.2 (3H, m); 14.6 (1H,s). |
| 67 | pale yellow oil | 0.98 (3H,t); 1.32 (3H,t); 1.6 (2H,m); 2.25 (6H,s); 2.5-3.4 (7H, |

TABLE 4-continued

Part (a)

| Compound No | Appearance | Proton Chemical Shift δ in ppm (CDCl₃) |
|---|---|---|
| | | m); 4.10 (2H,q); 7.00-7.25 (3H,m); 15.1 (1H,brs). |
| 68 | pale yellow oil | 0.98 (6H,t); 1.63 (4H,m); 2.24 (6H,s); 2.5-3.4 (7H,m); 4.01 (2H,q); 6.95-7.25 (3H,m); 14 (1H, brs). |
| 69 | pale yellow oil | 0.98 (3H,t); 1.63 (6H,s); 2.25 (6H,s); 2.5-3.4 (7H,m); 4.52 (2H,d,J=6.4 Hz); 5.25-5.44 (2H,m); 5.79-6.21 (1H,m); 6.90-7.25 (3H, m); 14.6 (1H,s). |
| 70 | pale brown solid; mp 183° C. | 1.32 (3H,t); 2.13-3.45 (23H,m); 4.13 (2H,q); 14.68 (1H,brs) |
| 71 | pale yellow oil | 1.12-1.40 (6H,m); 2.22 (3H,s); 2.30 (3H,s); 2.38 (3H,s); 2.63-2.99 (6H,m); 4.00-4.24 (3H,m); 5.93 (2H,m); 14.99 (1H,brs) |
| 72 | solid; mp >250° C. | Not recorded |
| 73 | pale yellow oil | 0.92 (3H,t); 1.10 (3H,t); 1.48 (2H,m); 2.23-3.76 (22H,m); 4.00 (2H,q); 7.45-8.09 (5H,m) |
| 74 | pale yellow oil | 0.99 (3H,t); 1.60 (2H,m); 2.10-4.90 (23H,m); 6.85 (1H,s); 13.95 (1H,brs) |
| 75 | pale brown solid; mp 132° C. | 0.99 (3H,t); 1.63 (2H,m); 2.22-4.94 (26H,m); 14.00 (1H,brs) |
| 76 | oil | 1.21 (3H,t); 2.22-4.89 (26H,m); 13.94 (1H,brs) |
| 77 | solid; mp 96° C. | Not recorded |
| 78 | solid; mp >250° C. | Not recorded |
| 79 | oil | 0.99 (6H,2×t); 1.69 (4H,m); 2.22-3.38 (22H,m); 4.02 (2H,t); 15.15 (1H,brs) |
| 80 | oil | 1.19 (3H,t); 2.22-2.83 (22H,m); 3.90 (3H,s); 14.71 (1H,brs) |
| 81 | oil | 1.09 (6H,2×t); 2.23-3.74 (22H,m); 4.02 (2H,q); 7.45-8.08 (5H,m) |
| 82 | oil | 1.01 (3H,t); 1.66 (2H,m); 2.23-4.06 (22H,m); 4.60 (2H,s); 5.48 (2H,s); 14.0 (1H,brs) |
| 83 | oil | 1.20 (3H,t); 1.77 (3H,d); 2.23-4.20 (22H,m); 4.47 (2H,d); 5.74 (2H,m); 14.0 (1H,brs) |
| 84 | pale green solid; mp 210° C. | Not recorded |
| 85 | pale brown solid; mp 240° C. | Not recorded |
| 86 | oil | 1.22 (3H,t); 2.22-4.22 (25H,m); 5.12 (2H,s); 14.04 (1H,s) |
| 87 | pale brown oil | 1.22 (3H,t); 2.31 (3H,s); 2.35-3.70 (5H,m); 3.95-4.45 (2H,m); 6.90-7.15 (3H,brs); 7.30-7.80 (3H, m); 8.00-8.30 (2H,m) |
| 88 | pale brown oil | 0.71-1.82 (34H,m); 2.22 (3H,s); 2.36 (6H,s); 1.99-2.70 (4H,m); 2.76-4.27 (11H,m); 4.07 (2H,q); 6.78 (2H,s) |
| 89 | oil | 0.8-1.4 (6H,m); 2.26 (3H,s); 2.45 (9H,s); 2.45-4.0 (9H,m); 6.92 (2H, s); 7.34 (2H,d); 8.0 (2H,d) |
| 90 | oil | 0.7-1.4 (6H,m); 2.25 (12H,s); 2.37 (6H,s); 2.37-4.0 (9H,m); 6.85 (4H, s) |
| 91 | oil | 0.8-1.3 (6H,m); 2.24 (3H,s); 2.42 (6H,s); 2.42-4.0 (12H,m+s); 6.85 (2H,s); 6.9 (2H,d); 7.95 (2H,d) |
| 92 | oil | 0.8-1.3 (6H,m); 2.24 (3H,s); 2.44 (6H,s); 2.45-4.2 (9H,m); 6.86 (2H, s); 7.96 (2H,d); 7.44 (2H,d) |
| 93 | oil | 1.01 (3H,t); 1.27 (3H,t); 2.16 (3H, s); 2.20 (3H,s); 2.38 (6H,s); 2.4- |
| 94 | oil | 4.3 (9H,m); 6.84 (2H,s) 0.99 (3H,t); 1.23 (12H,s+t); 2.24 (3H,s); 2.40 (6H,s); 2.45-4.3 (9H,m); 6.85 (2H,s) |
| 95 | solid; mp 138-142° C. | 0.9-1.4 (9H,m); 2.24 (3H,s); 2.38 (6H,s); 2.4-4.2 (11H,m); 4.62 (2H,s); 6.90 (2H,s) |

TABLE 4

Part (b)

| Compound No | Carbon-13 Chemical Shift δ in ppm (CDCl₃) |
|---|---|
| 1 | 11.26 (1C); 14.14 (1C); 14.68 (1C); 20.97 (2C); 33.91 (1C); 39-45 (2C); 70.26 (1C); 107.10 (1C); 122.79 (1C); 125.85 (1C); 128.50 (1C); 134.03 (1C); 137.22 (1C); 140.20 (1C); 166.53 1C); 184-195 (2C). |
| 2 | 11.22 (1C); 14.01 (1C); 19.07 (1C); 20.69 (1C); 20.86 (1C); 33.32 (1C); 39-45 (2C); 70.21 (1C); 107.05 (1C); 124.82 (1C); 126.99 (1C); 131.48 (1C); 135.22 (1C); 136.14 (1C); 137.39 (1C); 166.53 (1C); 184-195 (2C). |
| 3 | 11.32 (1C); 14.19 (1C); 18.85 (1C); 21.07 (1C); 21.18 (1C); 33.75 (1C); 39-45 (2C); 70.37 (1C); 107.21 (1C); 125.85 (1C); 127.47 (1C); 130.78 (1C); 132.35 (1C); 135.02 (1C); 140.31 (1C); 166.59 (1C); 184-195 (2C). |
| 4 | 11.27 (1C); 14.14 (1C); 21.13 (1C); 21.94 (2C); 33.75 (1C); 39-45 (2C); 70.37 (1C); 107.21 (1C); 126.77 (1C); 129.91 (2C); 136.36 (2C); 137.49 (1C); 166.75 (1C); 184-195 (2C). |
| 5 | 11.32 (1C); 14.25 (1C); 19.34 (1C); 19.88 (1C); 21.02 (1C); 37.38 (1C); 39-45 (2C); 70.26 (1C); 107.48 (1C); 123.90 (1C); 128.07 (1C); 130.02 (1C); 135.17 (1C); 136.84 (1C); 140.15 (1C); 166.34 (1C); 184-195 (2C). |
| 6 | 11.21 (1C); 14.09 (1C); 20.86 (2C); 21.29 (1C); 37.54 (1C); 39-45 (2C); 70.26 (1C); 107.27 (1C); 124.33 (2C); 128.56 (2C); 138.20 (2C); 142.42 (1C); 166.48 (1C); 184-195 (2C). |

EXAMPLE 22

This non-limiting Example illustrates the preparation of formulations of the compounds of the invention.

(a) Emulsifiable Concentrate

Compound No 7 was dissolved in toluene containing 7% v/v "Teric" N13 and 3% v/v "Kemmat" SC15B to give an emulsifiable concentrate which may be diluted with water to the required concentration to give an aqueous emulsion which may be applied by spraying.

("Teric" is a Trade Mark and "Teric" N13, is a product of ethoxylation of nonylphenol; "Kemmat" is a Trade Mark and "Kemmat" SC15B is a formulation of calcium dodecylbenzenesulfonate.)

(b) Aqueous Suspension

Compound No 7 (5 parts by weight) and "Dyapol" PT (1 part by weight) was added to an aqueous solution (94 parts by weight) of "Teric" N8 and the mixture was ball milled to produce a stable aqueous suspension which may be diluted with water to the required concentration to give an aqueous suspension which may be applied by spraying. ("Dyapol" is a Trade Mark and "Dyapol" PT is an anionic suspending agent; "Teric" N8 is a product of ethoxylation of nonylphenol.)

(c) Emulsifiable Concentrate

Compoiund No 7 (10 parts by weight), "Teric" N13 (5 parts by weight) and "Kemmat" SC15B (5 parts by weight) were dissolved in "Solvesso" 150 (80 parts by weight) to give an emulsifiable concentrate which may be diluted with water to the required concentration to give an aqueous emulsion which may be applied by spraying. ("Solvesso" is a Trade Mark and "Solvesso" 150 is a high boiling point aromatic petroleum fraction.)

(d) Dispersible Powder

Compound No 7 (10 parts by weight), "Matexil" DA/AC (3 parts by weight), "Aerosol" OT/B (1 part by weight) and china clay 298 (86 parts by weight) were blended and then milled to give a powder composition having a particle size below 50 microns. ("Matexil" is a Trade Mark and "Matexil" DA/AC is the disodium salt of a naphthalenesulfonic acid/formaldehyde condensate; "Aerosol" is a Trade Mark and "Aerosol" OT/B is a formulation of the dioctyl ester of sodium sulfosuccinic acid.)

(e) High Strength Concentrate

Compound No 7 (99 parts by weight), silica aerogel (0.5 parts by weight) and synthetic amorphous silica (0.5 parts by weight) were blended and ground in a hammer-mill to produce a powder having a particle size less than 200 microns.

(f) Dusting Powder

Compound No 7 (10 parts by weight), attapulgite (10 parts by weight) and pyrophyllite (80 parts by weight) were thoroughly blended and then ground in a hammer-mill to produce a powder of particle size less than 200 microns.

Emulsifiable concentrates and/or suspensions of the compounds of the invention were prepared essentially as described in part (a), (b) or (c) above and then diluted with water, optionally containing a surface active agent and/or oil, to give aqueous compositions of the required concentration which were used, as described in Examples 23 and 24, in the evaluation of the pre-emergence and post-emergence herbicidal activity of the compounds.

EXAMPLE 23

The pre-emergent herbicidal activity of the compounds of the invention formulated as described in Example 22 was assessed by the following procedure:

The seeds of the test species were sown in rows 2 cm deep in soil contained in seed boxes. The monocotyledonous plants and the dicotyledonous plants were sown in separate boxes and after sowing the two boxes were sprayed with the required quantity of a composition of the invention. Two duplicate seed boxes were prepared in the same manner but were not sprayed with a composition of the invention and were used for comparison purposes. All the boxes were placed in a glasshouse, lightly watered with an overhead spray to initiate germination and then sub-irrigated as required for optimum plant growth. After three weeks the boxes were removed from the glasshouse and the effects of the treatment was visually assessed. The results are presented in Table 5 where the damage to plants is rated on a scale of from 0 to 5 where 0 represents from 0 to 10% damage, 1 represents from 11 to 30% damage, 2 represents from 31 to 60% damage, 3 represents from 61 to 80% damage, 4 represents from 81 to 99% damage and 5 represents 100% kill. A dash (-) means that no experiment was carried out.

The names of the test plants are as follows:
Wh: Wheat
Ot: Wild Oats
Rg: Ryegrass
Jm: Japanese millet
P: Peas
Ip: Ipomea
Ms: Mustard
Sf: Sunflower

TABLE 5

PRE-EMERGENCE HERBICIDAL ACTIVITY

| Compound No | APPLICATION Rate (kg/ha) | Wh | Ot | Rg | Jm | P | Ip | Ms | Sf |
|---|---|---|---|---|---|---|---|---|---|
| 9 | 2.0 | 3 | 5 | 5 | 5 | 0 | 0 | 0 | 0 |
| 9 | 0.5 | 0 | 5 | 5 | 5 | 0 | 0 | 0 | 0 |
| 10 | 2.0 | 1 | 5 | 5 | 5 | 0 | 0 | 0 | 0 |
| 10 | 0.5 | 0 | 5 | 5 | 5 | 0 | 0 | 0 | 0 |
| 16 | 2.0 | 4 | 5 | 5 | 5 | 0 | 0 | 0 | 0 |
| 16 | 0.5 | 0 | 5 | 5 | 5 | 0 | 0 | 0 | 0 |
| 18 | 2.0 | 2 | 5 | 5 | 5 | 0 | 0 | 0 | 0 |
| 18 | 0.5 | 0 | 5 | 5 | 4 | 0 | 0 | 0 | 0 |
| 19 | 2.0 | 3 | 5 | 5 | 5 | 0 | 0 | 0 | 0 |
| 19 | 0.5 | 0 | 3 | 5 | 5 | 0 | 0 | 0 | 0 |
| 24 | 2.0 | 0 | 5 | 5 | 5 | 0 | 0 | 0 | 0 |
| 24 | 0.5 | 0 | 0 | 5 | 5 | 0 | 0 | 0 | 0 |
| 25 | 1.0 | 2 | 5 | 5 | 5 | 0 | 0 | 0 | 0 |
| 25 | 0.25 | 1 | 1 | 5 | 5 | 0 | 0 | 0 | 0 |
| 26 | 1.0 | 1 | 4 | 5 | 5 | 0 | 0 | 0 | 0 |
| 26 | 0.25 | 0 | 0 | 5 | 5 | 0 | 0 | 0 | 0 |
| 38 | 2.0 | 0 | 2 | 5 | 4 | 0 | 0 | 0 | 0 |
| 38 | 0.5 | 0 | 3 | 5 | 4 | 0 | 0 | 0 | 0 |
| 47 | 2.0 | 4 | 5 | 5 | 5 | 0 | 0 | 0 | 0 |
| 47 | 0.5 | 0 | 0 | 5 | 4 | 0 | 0 | 0 | 0 |
| 50 | 2.0 | 4 | 5 | 5 | 5 | 0 | 0 | 0 | 0 |
| 50 | 0.5 | 0 | 4 | 5 | 4 | 0 | 0 | 0 | 0 |
| 52 | 1.0 | 0 | 1 | 5 | 5 | 0 | 0 | 0 | 0 |
| 52 | 0.25 | 0 | 0 | 4 | 0 | 0 | 0 | 0 | 0 |
| 54 | 2.0 | 3 | 4 | 5 | 5 | 0 | 0 | 0 | 0 |
| 54 | 0.5 | 0 | 0 | 5 | 5 | 0 | 0 | 0 | 0 |
| 56 | 1.0 | 0 | 3 | 5 | 5 | 0 | 0 | 0 | 0 |
| 56 | 0.25 | 0 | 2 | 5 | 5 | 0 | 0 | 0 | 0 |
| 59 | 1.0 | 4 | 5 | 5 | 5 | 0 | 0 | 0 | 0 |
| 59 | 0.25 | 2 | 5 | 5 | 5 | 0 | 0 | 0 | 0 |
| 61 | 1.0 | 0 | 2 | 4 | 5 | 0 | 0 | 0 | 0 |
| 61 | 0.25 | 0 | 0 | 5 | 4 | 0 | 0 | 0 | 0 |
| 67 | 1.0 | 0 | 5 | 5 | 1 | 0 | 0 | 0 | 0 |
| 67 | 0.25 | 0 | 0 | 5 | 0 | 0 | 0 | 0 | 0 |
| 70 | 0.5 | 4 | 3 | 5 | 5 | 0 | 0 | 0 | 0 |
| 70 | 0.125 | 0 | 1 | 5 | 5 | 0 | 0 | 0 | 0 |
| 71 | 0.5 | 1 | 4 | 5 | 5 | 0 | 0 | 0 | 0 |
| 71 | 0.125 | 0 | 1 | 5 | 5 | 0 | 0 | 0 | 0 |
| 73 | 0.5 | 0 | 1 | 5 | 5 | 0 | 0 | 0 | 0 |
| 74 | 0.5 | 0 | 3 | 5 | 5 | 0 | 0 | 0 | 0 |
| 75 | 0.5 | 0 | 3 | 5 | 5 | 0 | 0 | 0 | 0 |
| 76 | 0.5 | 0 | 2 | 5 | 5 | 0 | 0 | 0 | 0 |
| 84 | 1.0 | 0 | 5 | 5 | 5 | 0 | 0 | 0 | 0 |

EXAMPLE 24

The post-emergent herbicidal activity of the compounds of the invention formulated as described in Example 22 was assessed by the following procedure.

The seeds of the test species were sown in rows 2 cm deep in soil contained in seed boxes. The monocotyledonous plants and the dicotyledonous plants were sown in separate seed boxes in duplicate. The four seed boxes were placed in a glasshouse, lightly watered with an overhead spray to initiate germination and then sub-irrigated as required for optimum plant growth. After the plants had grown to a height of about 10 to 12.5 cm one box of each of the monocotyledonous plants and the dicotyledonous plants was removed from the glasshouse and sprayed with the required quantity of a composition of the invention. After spraying the boxes were returned to the glass house for a further 3 weeks and the effect of treatment was visually assessed by comparison with the untreated controls. The results are presented in Table 6 where the damage to plants is rated on a scale of from 0 to 5 where 0 represents from 0 to 10% damage, 1 represents from 11 to 30% damage, 2 represents from 31 to 60% damage, 3 represents from 61 to 80% damage, 4 represents from 81 to 99% damage and 5 represents 100% kill. A dash (-) means that no experiment was carried out.

The names of the test plants are as follows:
Wh: Wheat
Ot: Wild Oats
Rg: Ryegrass
Jm: Japanese millet
P: Peas
Ip: Ipomea
Ms: Mustard
Sf: Sunflower

TABLE 6
POST-EMERGENCE HERBICIDAL ACTIVITY

| Compound No | APPLICATION Rate (kg/ha) | Wh | Ot | Rg | Jm | P | Ip | Ms | Sf |
|---|---|---|---|---|---|---|---|---|---|
| 1 | 2.0 | 1 | 5 | 5 | 5 | 0 | 0 | 0 | 0 |
| 1 | 0.5 | 0 | 3 | 4 | 4 | 0 | 0 | 0 | 0 |
| 2 | 2.0 | 1 | 4 | 5 | 5 | 0 | 0 | 0 | 0 |
| 2 | 0.5 | 0 | 2 | 4 | 5 | 0 | 0 | 0 | 0 |
| 3 | 2.0 | 0 | 3 | 5 | 5 | 0 | 0 | 0 | 0 |
| 5 | 2.0 | 3 | 2 | 5 | 5 | 0 | 0 | 0 | 0 |
| 5 | 0.5 | 0 | 4 | 4 | 4 | 0 | 0 | 0 | 0 |
| 6 | 2.0 | 3 | 5 | 5 | 5 | 0 | 0 | 0 | 0 |
| 6 | 0.5 | 0 | 4 | 5 | 5 | 0 | 0 | 0 | 0 |
| 7 | 2.0 | 2 | 5 | 5 | 5 | 0 | 0 | 0 | 0 |
| 7 | 0.5 | 2 | 5 | 5 | 5 | 0 | 0 | 0 | 0 |
| 7 | 0.25 | 0 | 5 | 5 | 5 | 0 | 0 | 0 | 0 |
| 7 | 0.125 | 0 | 5 | 5 | 4 | 0 | 0 | 0 | 0 |
| 8 | 2.0 | 1 | 5 | 5 | 5 | 0 | 0 | 0 | 0 |
| 8 | 0.5 | 0 | 3 | 5 | 5 | 0 | 0 | 0 | 0 |
| 11 | 2.0 | 0 | 4 | 5 | 5 | 0 | 0 | 0 | 0 |
| 11 | 0.5 | 0 | 3 | 3 | 4 | 0 | 0 | 0 | 0 |
| 15 | 2.0 | 1 | 5 | 5 | 5 | 0 | 0 | 0 | 0 |
| 15 | 0.5 | 1 | 5 | 5 | 5 | 0 | 0 | 0 | 0 |
| 15 | 0.25 | 0 | 4 | 5 | 5 | 0 | 0 | 0 | 0 |
| 15 | 0.125 | 0 | 5 | 5 | 4 | 0 | 0 | 0 | 0 |
| 16 | 2.0 | 4 | 5 | 5 | 5 | 0 | 0 | 0 | 0 |
| 16 | 0.5 | 2 | 5 | 5 | 5 | 0 | 0 | 0 | 0 |
| 18 | 2.0 | 5 | 5 | 5 | 5 | 0 | 0 | 0 | 0 |
| 18 | 0.5 | 3 | 5 | 5 | 5 | 0 | 0 | 0 | 0 |
| 19 | 2.0 | 4 | 5 | 5 | 5 | 0 | 0 | 0 | 0 |
| 19 | 0.5 | 0 | 5 | 5 | 5 | 0 | 0 | 0 | 0 |
| 22 | 1.0 | 0 | 5 | 5 | 5 | 0 | 0 | 0 | 0 |
| 22 | 0.25 | 0 | 5 | 5 | 5 | 0 | 0 | 0 | 0 |
| 24 | 2.0 | 3 | 5 | 5 | 5 | 0 | 0 | 0 | 0 |
| 24 | 0.5 | 0 | 5 | 5 | 4 | 0 | 0 | 0 | 0 |
| 25 | 1.0 | 2 | 5 | 5 | 5 | 0 | 0 | 0 | 0 |
| 25 | 0.25 | 0 | 5 | 5 | 5 | 0 | 0 | 0 | 0 |
| 26 | 1.0 | 0 | 5 | 5 | 5 | 0 | 0 | 0 | 0 |
| 26 | 0.25 | 0 | 4 | 5 | 4 | 0 | 0 | 0 | 0 |
| 28 | 1.0 | 0 | 5 | 5 | 5 | 0 | 0 | 0 | 0 |
| 28 | 0.25 | 0 | 5 | 5 | 4 | 0 | 0 | 0 | 0 |
| 36 | 1.0 | 2 | 5 | 5 | 5 | 0 | 0 | 0 | 0 |
| 36 | 0.25 | 0 | 5 | 5 | 5 | 0 | 0 | 0 | 0 |
| 38 | 2.0 | 3 | 5 | 5 | 5 | 0 | 0 | 0 | 0 |
| 38 | 0.5 | 1 | 5 | 4 | 4 | 0 | 0 | 0 | 0 |
| 39 | 1.0 | 2 | 5 | 5 | 5 | 0 | 0 | 0 | 0 |
| 39 | 0.25 | 0 | 5 | 5 | 5 | 0 | 0 | 0 | 0 |
| 40 | 1.0 | 3 | 5 | 5 | 5 | 0 | 0 | 0 | 0 |
| 40 | 0.25 | 0 | 5 | 5 | 5 | 0 | 0 | 0 | 0 |
| 40 | 0.125 | 0 | 4 | 5 | 5 | 0 | 0 | 0 | 0 |
| 41 | 1.0 | 0 | 5 | 5 | 5 | 0 | 0 | 0 | 0 |
| 41 | 0.25 | 0 | 4 | 5 | 5 | 0 | 0 | 0 | 0 |
| 46 | 1.0 | 4 | 5 | 5 | 5 | 0 | 0 | 0 | 0 |
| 46 | 0.25 | 0 | 5 | 5 | 5 | 0 | 0 | 0 | 0 |
| 47 | 2.0 | 3 | 5 | 5 | 5 | 0 | 0 | 0 | 0 |
| 47 | 0.5 | 0 | 5 | 5 | 5 | 0 | 0 | 0 | 0 |
| 50 | 2.0 | 4 | 5 | 5 | 5 | 0 | 0 | 0 | 0 |
| 50 | 0.5 | 0 | 4 | 5 | 5 | 0 | 0 | 0 | 0 |
| 51 | 2.0 | 4 | 5 | 5 | 5 | 0 | 0 | 0 | 0 |
| 51 | 0.5 | 0 | 4 | 5 | 5 | 0 | 0 | 0 | 0 |
| 52 | 1.0 | 0 | 5 | 5 | 5 | 0 | 0 | 0 | 0 |
| 52 | 0.25 | 0 | 4 | 5 | 5 | 0 | 0 | 0 | 0 |
| 53 | 1.0 | 0 | 5 | 5 | 5 | 0 | 0 | 0 | 0 |
| 53 | 0.25 | 0 | 3 | 4 | 4 | 0 | 0 | 0 | 0 |
| 54 | 2.0 | 2 | 5 | 5 | 5 | 0 | 0 | 0 | 0 |
| 54 | 0.5 | 0 | 3 | 4 | 5 | 0 | 0 | 0 | 0 |
| 55 | 0.25 | 5 | 5 | 5 | 5 | 0 | 0 | 0 | 0 |
| 55 | 0.125 | 3 | 5 | 5 | 5 | 0 | 0 | 0 | 0 |
| 57 | 0.25 | 1 | 5 | 5 | 5 | 0 | 0 | 0 | 0 |
| 57 | 0.125 | 1 | 4 | 4 | 5 | 0 | 0 | 0 | 0 |
| 58 | 1.0 | 4 | 5 | 5 | 5 | 0 | 0 | 0 | 0 |
| 58 | 0.25 | 3 | 5 | 5 | 5 | 0 | 0 | 0 | 0 |
| 59 | 1.0 | 5 | 5 | 5 | 5 | 0 | 0 | 0 | 0 |
| 59 | 0.25 | 3 | 5 | 5 | 5 | 0 | 0 | 0 | 0 |
| 60 | 2.0 | 5 | 5 | 5 | 5 | 0 | 0 | 0 | 0 |
| 60 | 0.5 | 3 | 5 | 5 | 5 | 0 | 0 | 0 | 0 |
| 61 | 1.0 | 3 | 5 | 5 | 5 | 0 | 0 | 0 | 0 |
| 61 | 0.25 | 1 | 5 | 5 | 5 | 0 | 0 | 0 | 0 |
| 62 | 1.0 | 5 | 5 | 5 | 5 | 0 | 0 | 0 | 0 |
| 62 | 0.25 | 2 | 5 | 5 | 5 | 0 | 0 | 0 | 0 |
| 62 | 0.125 | 1 | 5 | 5 | 5 | 0 | 0 | 0 | 0 |
| 63 | 1.0 | 0 | 5 | 5 | 5 | 0 | 0 | 0 | 0 |
| 63 | 0.25 | 0 | 4 | 4 | 4 | 0 | 0 | 0 | 0 |
| 64 | 2.0 | 0 | 5 | 5 | 5 | 0 | 0 | 0 | 0 |
| 64 | 0.5 | 1 | 5 | 5 | 5 | 0 | 0 | 0 | 0 |
| 66 | 2.0 | 2 | 5 | 5 | 5 | 0 | 0 | 0 | 0 |
| 66 | 0.5 | 0 | 5 | 5 | 5 | 0 | 0 | 0 | 0 |
| 67 | 1.0 | 0 | 5 | 5 | 5 | 0 | 0 | 0 | 0 |
| 67 | 0.25 | 0 | 4 | 4 | 4 | 0 | 0 | 0 | 0 |
| 70 | 0.5 | 4 | 5 | 5 | 5 | 0 | 0 | 0 | 0 |
| 70 | 0.125 | 0 | 4 | 3 | 5 | 0 | 0 | 0 | 0 |
| 71 | 0.5 | 0 | 5 | 5 | 5 | 0 | 0 | 0 | 0 |
| 71 | 0.125 | 0 | 3 | 5 | 5 | 0 | 0 | 0 | 0 |
| 72 | 0.5 | 1 | 5 | 5 | 5 | 0 | 0 | 0 | 0 |
| 72 | 0.125 | 0 | 5 | 5 | 5 | 0 | 0 | 0 | 0 |
| 73 | 0.5 | 0 | 4 | 5 | 5 | 0 | 0 | 0 | 0 |
| 73 | 0.125 | 0 | 4 | 5 | 5 | 0 | 0 | 0 | 0 |
| 74 | 0.5 | 0 | 4/5 | 5 | 5 | 0 | 0 | 0 | 0 |
| 74 | 0.125 | 0 | 4/5 | 5 | 5 | 0 | 0 | 0 | 0 |
| 75 | 0.5 | 0 | 4 | 5 | 5 | 0 | 0 | 0 | 0 |
| 75 | 0.125 | 0 | 3 | 4 | 5 | 0 | 0 | 0 | 0 |
| 76 | 0.5 | 2 | 5 | 5 | 5 | 0 | 0 | 0 | 0 |
| 76 | 0.125 | 0 | 0 | 5 | 5 | 0 | 0 | 0 | 0 |
| 84 | 1 | 0 | 5 | 5 | 5 | 0 | 0 | 0 | 0 |
| 84 | 0.125 | 0 | 2 | 1 | 0 | 0 | 0 | 0 | 0 |

EXAMPLE 25

The compounds were formulated for test by mixing an appropriate amount with 5 ml of an emulsion prepared by diluting 160 ml of a solution containing 21.9 g per liter of "Span" 80 and 78.2 g per liter of "Tween" 20 in methylcyclohexanone to 500 ml with water. "Span" 80 is a Trade Mark for a surface-active agent comprising sorbitan monolaurate. "Tween" 20 is a Trade Mark for a surface-active agent comprising a condensate of sorbitan monolaurate with 20 molar proportions of ethylene oxide. Each 5 ml emulsion containing a test compound was then diluted to 40 ml with water and sprayed on to young pot plants (post-emergence test) of the species named in Table 7 below. Damage to test plants was assessed after 14 days on a scale of 0 to 5 where 0 is 0 to 20% damage and 5 is complete kill. In a test for pre-emergence herbicidal activity, seeds of the test plants were sown in a shallow slit formed in the surface of soil in fibre trays. The surface was then levelled and sprayed, and fresh soil then spread thinly over the sprayed surface. Assessment of herbicidal damage was carried out after 21 days using the same scale of 0 to 5 as the post-emergence test. In both cases the degree of herbicidal damage was assessed by comparison with untreated control plants. The results are given in Table 7 below. A dash (-) means that no experiment was carried out.

The names of the test plants were as follows:
Sb: Sugar beet
Rp: Rape
Ct: Cotton
Sy: Soy bean
Mz: Maize
Ww: Winter wheat
Rc: Rice
Sn: *Senecio vulgaris*
Ip: *Ipomea purpurea*
Am: *Amaranthus retroflexus*
Pi: *Polygonum aviculare*
Ca: *Chenopodium album*
Ga: *Galium aparine*
Xa: *Xanthium pensylvanicum*
Ab: *Abutilon theophrasti*
Co: *Cassia obtusifolia*
Av: *Avena fatua*
Dg: *Digitaria sanguinalis*
Al: *Alopecurus myosuroides*
St: *Setaria viridis*
Ec: *Echinochloa crus-galli*
Sh: *Sorghum halepense*
Ag: *Agropyron repens*
Cn: *Cyperus rotundas* per liter of "Span" 80 and 78.2 g per liter of "Tween" 20 in methylcyclohexanone to 500 ml with water. "Span" 80 is a Trade Mark for a surface-active agent comprising sorbitan monolaurate. "Tween" 20 is a Trade Mark for a surface-active agent comprising a condensate or sorbitan monolaurate with 20 molar proportions of ethylene oxide. Each 5 ml emulsion containing a test compound was then diluted to 40 ml with water and sprayed on to young pot plants (post-emergence test) of the species named in Table 8 below. Damage to test plants was assessed after 26 days on a scale of 0 to 9 where 0 is 0 to 10% damage and 9 is complete kill. The degree of herbicidal damage was assessed by comparison with untreated control plants and the results are given in Table 8 below. A dash (-) means that no experiment was carried out.

The names of the test plants were as follows:
Ww: winter wheat
Br: spring barley
Av: *Avena fatua*
Al: *Alopecurus myosuroides*
St: *Setaria viridis*

TABLE 8
POST-EMERGENCE HERBICIDAL ACTIVITY

| Compound No | APPLICATION Rate (kg/ha) | Ww | Br | Av | Al | St |
|---|---|---|---|---|---|---|
| 5 | 0.10 | 0 | 0 | 9 | 8 | 6 |
| 5 | 0.20 | 1 | 1 | 9 | 9 | 8 |
| 5 | 0.40 | 0 | 1 | 9 | 9 | 9 |
| 7 | 0.03 | 0 | 1 | 8 | 8 | 8 |
| 7 | 0.04 | 0 | 0 | 9 | 9 | 8 |
| 7 | 0.08 | 1 | 1 | — | — | — |
| 7 | 0.16 | 0 | 1 | — | — | — |
| 10 | 0.04 | 0 | 1 | 9 | 9 | 8 |
| 10 | 0.08 | 1 | 2 | — | — | — |
| 10 | 0.16 | 2 | 5 | — | — | — |
| 15 | 0.08 | 0 | 1 | 9 | 6 | 7 |
| 15 | 0.16 | 1 | 1 | — | — | — |

TABLE 7
PART A

| Compound No | APPLICATION Method | Rate (kg/ha) | Sb | Rp | Ct | Sy | Mz | Ww | Rc | Sn | Ip | Am | Pi | Ca |
|---|---|---|---|---|---|---|---|---|---|---|---|---|---|---|
| 7 | POST | 1.9 | 0 | 0 | 0 | — | 5 | 3 | 4 | 0 | 0 | — | 0 | 0 |
| 7 | POST | 0.5 | 0 | 0 | 0 | — | 5 | 0 | 4 | 0 | 1 | — | 0 | 0 |
| 5 | POST | 2.0 | — | — | — | — | — | 2 | — | — | — | — | — | — |
| 5 | POST | 1.0 | — | — | — | — | — | 1 | — | — | — | — | — | — |
| 5 | POST | 0.5 | — | — | — | — | — | 0 | — | — | — | — | — | — |
| 5 | POST | 0.25 | — | — | — | — | — | 0 | — | — | — | — | — | — |
| 11 | POST | 2.0 | — | — | — | — | — | 1 | — | — | — | — | — | — |
| 11 | POST | 1.0 | — | — | — | — | — | 1 | — | — | — | — | — | — |
| 11 | POST | 0.5 | — | — | — | — | — | 0 | — | — | — | — | — | — |
| 11 | POST | 0.25 | — | — | — | — | — | 0 | — | — | — | — | — | — |

TABLE 7
PART B

| Compound No | APPLICATION Method | Rate (kg/ha) | Ga | Xa | Ab | Co | Av | Dg | Al | St | Ec | Sh | Ag | Cn |
|---|---|---|---|---|---|---|---|---|---|---|---|---|---|---|
| 7 | POST | 1.9 | 0 | 0 | 0 | 0 | 5 | 3 | 5 | 4 | 5 | 4 | 2 | 0 |
| 7 | POST | 0.5 | 0 | 0 | 0 | 0 | 4 | 3 | 4 | 5 | 5 | 3 | 0 | 0 |
| 5 | POST | 2.0 | — | — | — | — | 5 | — | 4 | 5 | — | — | — | — |
| 5 | POST | 1.0 | — | — | — | — | 4 | — | 4 | 4 | — | — | — | — |
| 5 | POST | 0.5 | — | — | — | — | 4 | — | 4 | 3 | — | — | — | — |
| 5 | POST | 0.25 | — | — | — | — | 4 | — | 4 | 3 | — | — | — | — |
| 11 | POST | 2.0 | — | — | — | — | 5 | — | 4 | 4 | — | — | — | — |
| 11 | POST | 1.0 | — | — | — | — | 4 | — | 4 | 4 | — | — | — | — |
| 11 | POST | 0.5 | — | — | — | — | 4 | — | 4 | 4 | — | — | — | — |
| 11 | POST | 0.25 | — | — | — | — | 4 | — | 4 | 3 | — | — | — | — |

EXAMPLE 26

This Example illustrates the selective herbicidal activity of compounds of the invention.

The compounds were formulated for test by mixing an appropriate amount with 5 ml of an emulsion prepared by diluting 160 ml of a solution containing 21.8 g

TABLE 8-continued

POST-EMERGENCE HERBICIDAL ACTIVITY

| Compound No | APPLICATION Rate (kg/ha) | Ww | Br | Av | Al | St |
|---|---|---|---|---|---|---|
| 15 | 0.32 | 1 | 0 | — | — | — |
| 18 | 0.03 | 0 | 1 | 9 | 9 | 8 |
| 18 | 0.04 | 0 | 1 | 9 | 8 | 8 |
| 18 | 0.08 | — | — | 9 | 9 | 9 |
| 18 | 0.16 | 0 | 0 | — | — | — |
| 60 | 0.04 | — | — | 9 | 8 | 9 |
| 60 | 0.06 | 0 | 6 | 9 | 8 | 9 |
| 60 | 0.08 | 0 | 5 | 9 | 8 | 9 |
| 60 | 0.16 | 0 | 8 | — | — | — |
| 60 | 0.32 | 0 | 9 | — | — | — |
| 62 | 0.02 | — | — | 9 | 7 | 9 |
| 62 | 0.04 | — | — | 9 | 9 | 9 |
| 62 | 0.06 | 0 | 5 | 9 | 9 | 9 |
| 62 | 0.08 | 0 | 7 | 9 | 9 | 9 |
| 62 | 0.16 | 0 | 9 | — | — | — |
| 62 | 0.32 | 0 | 9 | — | — | — |
| 72 | 0.04 | — | — | 9 | 9 | 9 |
| 72 | 0.06 | 0 | 0 | 9 | 9 | 9 |
| 72 | 0.08 | 0 | 3 | 9 | 9 | 9 |
| 72 | 0.16 | 0 | 7 | — | — | — |
| 72 | 0.32 | 1 | 9 | — | — | — |
| 78 | 0.04 | — | — | 9 | 7 | 8 |
| 78 | 0.06 | 0 | 0 | 9 | 8 | 9 |
| 78 | 0.08 | 0 | 2 | 9 | 9 | 9 |
| 78 | 0.16 | 0 | 7 | — | — | — |
| 78 | 0.32 | 0 | 9 | — | — | — |

We claim:

1. A compound of the formula I wherein:
$R^1$ is selected from the group consisting of: hydrogen; $C_2$ to $C_6$ alkanoyl; benzoyl and substituted benzoyl wherein the benzene ring is substituted with from 1 to 3 substituents selected from the group consisting of halogen, nitro, $C_1$ to $C_6$ alkyl and $C_1$ to $C_6$ alkoxy; and an inorganic or organic cation selected from the alkali metal ions, the alkaline earth metal ions, transition metal ions and the ammonium ion $R^4R^5R^6R^7N^\oplus$ wherein $R^4$, $R^5$, $R^6$ and $R^7$ are independently selected from the group consisting of: hydrogen; $C_1$ to $C_{10}$ alkyl; and substituted $C_1$ to $C_{10}$ alkyl wherein the alkyl group is substituted with a substituent selected from the group consisting of hydroxy and $C_1$ to $C_6$ alkoxy;

$R^2$ is selected from the group consisting of: $C_1$ to $C_6$ alkyl; $C_2$ to $C_6$ alkenyl; $C_2$ to $C_6$ alkynyl; $C_1$ to $C_6$ haloalkyl; $C_2$ to $C_6$ haloalkenyl; $C_1$ to $C_6$ alkyl substituted with $C_1$ to $C_6$ alkoxy; $C_1$ to $C_6$ alkyl substituted with $C_1$ to $C_6$ alkylthio; and benzyl and substituted benzyl wherein the benzene ring is substituted with from one to three substituents selected from the group consisting of halogen, nitro and $C_1$ to $C_6$ alkyl;

$R^3$ is selected from the group consisting of $C_1$ to $C_6$ alkyl; and n is an integer chosen from 0 to 2.

2. A compound according to claim 1 wherein:
$R^1$ is selected from the group consisting of hydrogen, acetyl, butyryl, benzoyl, halobenzoyl, methylbenzoyl, methoxybenzoyl, nitrobenzoyl, trimethylbenzoyl, dinitrobenzoyl, the cations of the alkali metals sodium and potassium; the cations of the alkaline earth metals magnesium, calcium and barium, the cations of the transition metals manganese, copper, zinc, iron, nickel, cobalt and silver, the ammonium ion, and the tri- and tetra-alkyl ammonium ions wherein alkyl is selected from $C_1$ to $C_6$ alkyl and $C_1$ to $C_6$ hydroxyalkyl;

$R^2$ is selected from the group consisting of ethyl, n-propyl, n-butyl, allyl, propargyl, 2-fluoroethyl, 2-chloroallyl, methylthiomethyl, benzyl, halobenzyl, methylbenzyl and nitrobenzyl;

$R^3$ is selected from the group consisting of methyl ethyl and n-propyl; and n is an integer selected from 0 to 2.

3. A compound according to claim 2 wherein:
$R^1$ is selected from the group consisting of hydrogen, benzoyl and the cations of the alkali metals sodium and potassium;

$R^2$ is selected from the group consisting of ethyl, n-propyl and allyl;

$R^3$ is selected from ethyl and n-propyl; and n is an integer selected from 0 to 2.

4. A compound according to claim 3 of formula wherein:
$R^1$ is selected from hydrogen, sodium and potassium;
$R^2$ is selected from ethyl and allyl; and
$R^3$ is selected from ethyl and n-propyl.

5. A compound according to claim 3 of formula wherein:
$R^1$ is selected from hydrogen, sodium and potassium;
$R^2$ is selected from ethyl and allyl; and
$R^3$ is selected from ethyl and n-propyl.

6. A compound according to claim 3 of formula wherein:
$R^1$ is selected from hydrogen, sodium and potassium;
$R^2$ is selected from ethyl and allyl; and
$R^3$ is selected from ethyl and n-propyl.

7. A compound according to claim 3 selected from the group consistng of:

2-[1-(ethoxyimino)propyl]-3-hydroxy-5-mesitylcyclohex-2-en-1-one;

2-[1-(ethoxyimino)propyl]-3-hydroxy-5-(2,3,4,6-tetramethylphenyl)cyclohex-2-en-1-one;

2-[1-(ethoxyimino)butyl]-3-hydroxy-5-mesitylcyclohex-2-en-1-one;

2-[1-(ethoxyimino)propyl]-3-hydroxy-5-(2,3,4,5,6-pentamethylphenyl)cyclohex-2-en-1-one;

2-[1-(ethoxyimino)butyl]-3-hydroxy-5-(2,3,4,5,6-pentamethylphenyl)cyclohex-2-en-1-one;

2-[1-(ethoxyimino)propyl]-3-hydroxy-5-(2,3,4,5,6-pentamethylphenyl)cyclohex-2-en-1-one sodium salt; and 2-[1-(ethoxyimino)butyl]-3-hydroxy-5-(2,3,4,5,6-pentamethylphenyl)cyclohex-2-en-1-one sodium salt.

8. A herbicidal composition comprising as active ingredient a herbicidally effective amount of a compound as defined according to claim 1 and a carrier therefor.

9. A process for severely damaging or killing unwanted plants which process comprises applying to said plants, or to the growth medium of said plants, an effective amount of a compound as defined according to claim 1.

10. A process for selectively controlling the growth of monocotyledonous weeds in dicotyledonous crops which process comprises applying to said crop, or to the growth medium of said crop, a compound as defined according to claim 1 in an amount sufficient to severely damage or kill said weeds but insufficient to substantially damage said crop.

11. A process for selectively controlling the growth of monocotyledonous weeds in cultivated crops which process comprises applying to said crop or to the growth medium of said crop a compound as defined according to claim 1 in an amount sufficient to severely damage or kill said weeds but insufficient to substantially damage said crop.

12. A process according to claim 9 wherein the compound is applied at a rate in the range of from 0.005 to 20 kilograms per hectare.

13. A process according to claim 10 wherein the compound is applied at a rate in the range from 0.01 to 5 kilograms per hectare.

14. A process according to claim 11 wherein the compound is applied at a rate in the range of from 0.01 to 5 kilograms per hectare.

* * * * *